(12) United States Patent
Sulakova et al.

(10) Patent No.: US 11,670,461 B2
(45) Date of Patent: Jun. 6, 2023

(54) SOLID ELECTROLYTIC CAPACITOR FOR USE AT HIGH VOLTAGES

(71) Applicant: AVX Corporation, Fountain Inn, SC (US)

(72) Inventors: Romana Sulakova, Usti nad Orlici (CZ); Miloslav Uher, Lanskroun (CZ); Jan Petrzilek, Usti nad Orlici (CZ)

(73) Assignee: KYOCERA AVX Components Corporation

( * ) Notice: Subject to any disclaimer, the term of this patent is extended or adjusted under 35 U.S.C. 154(b) by 0 days.

(21) Appl. No.: 17/024,932

(22) Filed: Sep. 18, 2020

(65) Prior Publication Data

US 2021/0082631 A1    Mar. 18, 2021

Related U.S. Application Data

(60) Provisional application No. 62/901,915, filed on Sep. 18, 2019.

(51) Int. Cl.
| | |
|---|---|
| *H01G 9/15* | (2006.01) |
| *H01G 9/052* | (2006.01) |
| *H01G 9/028* | (2006.01) |
| *H01G 9/042* | (2006.01) |
| *H01G 9/08* | (2006.01) |

(Continued)

(52) U.S. Cl.
CPC ............. *H01G 9/15* (2013.01); *C07D 495/04* (2013.01); *C08L 65/00* (2013.01); *H01G 9/028* (2013.01); *H01G 9/042* (2013.01); *H01G 9/052* (2013.01); *H01G 9/08* (2013.01); *H01G 13/00* (2013.01); *C08L 2203/20* (2013.01); *C08L 2205/025* (2013.01); *C08L 2205/14* (2013.01)

(58) Field of Classification Search
None
See application file for complete search history.

(56) References Cited

U.S. PATENT DOCUMENTS

| | | | |
|---|---|---|---|
| 3,889,357 A | 6/1975 | Millard et al. | |
| 5,111,327 A | 5/1992 | Blohm et al. | |

(Continued)

FOREIGN PATENT DOCUMENTS

| | | | |
|---|---|---|---|
| CN | 102768903 A | 11/2012 | |
| CN | 103854868 A | 6/2014 | |

(Continued)

OTHER PUBLICATIONS

U.S. Appl. No. 10/186,382, filed Jan. 2019, Uher et al.

(Continued)

*Primary Examiner* — Dion R. Ferguson
(74) *Attorney, Agent, or Firm* — Dority & Manning, P.A.

(57) ABSTRACT

A capacitor that is capable of exhibiting good electrical properties even under a variety of conditions is provided. More particularly, the capacitor contains a sintered porous anode body, a dielectric that overlies the anode body, and a solid electrolyte that overlies the dielectric. The solid electrolyte contains an inner layer and an outer layer, wherein the inner layer is formed from an in situ-polymerized conductive polymer and the outer layer is formed from pre-polymerized conductive polymer particles. Further, the in-situ polymerized conductive polymer is formed from an alkylated thiophene monomer.

22 Claims, 5 Drawing Sheets

(51) Int. Cl.
  *C07D 495/04* (2006.01)
  *C08L 65/00* (2006.01)
  *H01G 13/00* (2013.01)

(56) References Cited

U.S. PATENT DOCUMENTS

| | | |
|---|---|---|
| 5,457,862 A | 10/1995 | Sakata et al. |
| 5,473,503 A | 12/1995 | Sakata et al. |
| 5,729,428 A | 3/1998 | Sakata et al. |
| 5,812,367 A | 9/1998 | Kudoh et al. |
| 6,197,252 B1 | 3/2001 | Bishop et al. |
| 6,369,239 B2 | 4/2002 | Rauchschwalbe et al. |
| 6,430,033 B1 | 8/2002 | Mitsui et al. |
| 6,528,662 B2 | 3/2003 | Jonas |
| 6,635,729 B1 | 10/2003 | Groenendaal et al. |
| 6,674,635 B1 | 1/2004 | Fife et al. |
| 6,771,488 B2 | 8/2004 | Takagi et al. |
| 6,805,816 B1 | 10/2004 | Groenendaal et al. |
| 6,891,016 B2 | 5/2005 | Reuter et al. |
| 6,987,663 B2 | 1/2006 | Merker et al. |
| 7,008,562 B2 | 3/2006 | Jonas et al. |
| 7,053,174 B2 | 5/2006 | Kirchmeyer et al. |
| 7,102,016 B2 | 9/2006 | Reuter |
| 7,118,690 B2 | 10/2006 | Wessling et al. |
| 7,154,740 B2 | 12/2006 | Merker et al. |
| 7,154,742 B1 | 12/2006 | Hahn et al. |
| 7,183,419 B2 | 2/2007 | Heuer et al. |
| 7,199,251 B2 | 4/2007 | Kirchmeyer et al. |
| 7,288,663 B2 | 10/2007 | Kirchmeyer et al. |
| 7,341,801 B2 | 3/2008 | Reuter et al. |
| 7,358,326 B2 | 4/2008 | Heuer et al. |
| 7,363,511 B2 | 4/2008 | Kiiveri |
| 7,377,947 B2 | 5/2008 | Merker et al. |
| 7,411,779 B2 | 8/2008 | Merker et al. |
| 7,449,588 B2 | 11/2008 | Jonas et al. |
| 7,497,879 B2 | 3/2009 | Kakuma et al. |
| 7,515,396 B2 | 4/2009 | Biler |
| 7,563,290 B2 | 7/2009 | Qiu et al. |
| 7,585,983 B2 | 9/2009 | Reuter et al. |
| 7,621,970 B2 | 11/2009 | Furusawa et al. |
| 7,649,730 B2 | 1/2010 | Jones et al. |
| 7,750,099 B2 | 7/2010 | Chikusa et al. |
| 7,771,621 B2 | 8/2010 | Kuramoto et al. |
| 7,785,493 B2 | 8/2010 | Jonas et al. |
| 7,859,829 B2 | 12/2010 | Kakuma et al. |
| 7,872,858 B2 | 1/2011 | Kakuma et al. |
| 7,923,475 B2 | 4/2011 | Jonas et al. |
| 7,938,866 B2 | 5/2011 | Biler |
| 7,938,986 B2 | 5/2011 | Elschner et al. |
| 7,951,901 B2 | 5/2011 | Reuter et al. |
| 7,972,534 B2 | 7/2011 | Merker et al. |
| 7,973,180 B2 | 7/2011 | Morita et al. |
| 7,990,683 B2 | 8/2011 | Qiu et al. |
| 7,990,684 B2 | 8/2011 | Sugihara et al. |
| 7,994,345 B2 | 8/2011 | Brassat et al. |
| 8,058,135 B2 | 11/2011 | Merker et al. |
| 8,090,548 B2 | 1/2012 | Abdennadher et al. |
| 8,125,768 B2 * | 2/2012 | Horacek ............... H01G 11/56 361/532 |
| 8,195,490 B2 | 6/2012 | Tambe et al. |
| 8,224,681 B2 | 7/2012 | Tambe et al. |
| 8,310,815 B2 | 11/2012 | Freeman et al. |
| 8,313,538 B2 | 11/2012 | Merker et al. |
| 8,323,361 B2 | 12/2012 | Freeman et al. |
| 8,334,331 B2 | 12/2012 | Elschner et al. |
| 8,364,511 B2 | 1/2013 | Tambe et al. |
| 8,419,809 B2 | 4/2013 | Ishimaru |
| 8,420,671 B2 | 4/2013 | Reuter et al. |
| 8,426,542 B2 | 4/2013 | Sugihara et al. |
| 8,451,588 B2 | 5/2013 | Biler |
| 8,456,803 B2 | 6/2013 | Merker et al. |
| 8,462,484 B2 | 6/2013 | Kakuma et al. |
| 8,493,713 B2 * | 7/2013 | Biler ............... H01G 9/042 361/525 |
| 8,535,812 B2 | 9/2013 | Totsuka et al. |
| 8,576,543 B2 * | 11/2013 | Biler ............... H01G 9/15 361/523 |
| 8,592,520 B2 | 11/2013 | Kirchmeyer et al. |
| 8,663,505 B2 | 3/2014 | Loevenich et al. |
| 8,696,767 B2 | 4/2014 | Shibuya |
| 8,696,768 B2 | 4/2014 | Merker et al. |
| 8,699,208 B2 | 4/2014 | Merker et al. |
| 8,702,817 B2 | 4/2014 | Ishimaru |
| 8,721,928 B2 | 5/2014 | Jonas et al. |
| 8,721,929 B2 | 5/2014 | Loevenich et al. |
| 8,771,381 B2 | 7/2014 | Chen et al. |
| 8,808,403 B2 | 8/2014 | Qiu et al. |
| 8,824,121 B2 | 9/2014 | Biler |
| 8,837,114 B2 | 9/2014 | Kamiyama et al. |
| 8,882,856 B2 | 11/2014 | Intelmann et al. |
| 8,902,567 B2 | 12/2014 | Chacko |
| 8,936,735 B2 | 1/2015 | Guntermann et al. |
| 8,940,191 B2 | 1/2015 | Nobuta et al. |
| 9,030,807 B2 | 5/2015 | Chacko et al. |
| 9,034,211 B2 | 5/2015 | Megura et al. |
| 9,053,839 B2 | 6/2015 | Lövenich |
| 9,058,916 B2 | 6/2015 | Meguro et al. |
| 9,087,994 B2 | 7/2015 | Lövenich et al. |
| 9,111,680 B2 | 8/2015 | Intelmann et al. |
| 9,208,954 B2 | 12/2015 | Matsuura et al. |
| 9,236,191 B2 | 1/2016 | Chacko et al. |
| 9,251,961 B2 | 2/2016 | Merker et al. |
| 9,287,051 B2 | 3/2016 | Aoyama et al. |
| 9,287,053 B2 | 3/2016 | Ishimaru |
| 9,296,921 B2 | 3/2016 | Okamoto et al. |
| 9,312,074 B2 | 4/2016 | Chacko et al. |
| 9,343,239 B2 | 5/2016 | Zhang et al. |
| 9,362,055 B2 | 6/2016 | Sugihara et al. |
| 9,373,448 B2 | 6/2016 | Majima et al. |
| 9,378,896 B2 | 6/2016 | Sugimura |
| 9,384,866 B2 | 7/2016 | Jibiki et al. |
| 9,406,445 B2 | 8/2016 | Petrzilek et al. |
| 9,455,092 B2 | 9/2016 | Sugawara et al. |
| 9,460,860 B2 | 10/2016 | Sugihara et al. |
| 9,466,432 B2 | 10/2016 | Aoyama et al. |
| 9,472,348 B2 | 10/2016 | Takatani et al. |
| 9,502,183 B2 | 11/2016 | Saulter et al. |
| 9,508,491 B2 | 11/2016 | Merker et al. |
| 9,514,888 B2 | 12/2016 | Merker et al. |
| 9,514,889 B2 | 12/2016 | Asteman et al. |
| 9,530,568 B2 | 12/2016 | Takatani et al. |
| 9,589,734 B2 | 3/2017 | Koseki et al. |
| 9,589,738 B2 | 3/2017 | Sugihara et al. |
| 9,595,396 B2 | 3/2017 | Matsuura et al. |
| 9,640,325 B2 | 5/2017 | Tagawa et al. |
| 9,672,989 B2 | 6/2017 | Uher et al. |
| 9,718,905 B2 | 8/2017 | Yano et al. |
| 9,754,697 B2 | 9/2017 | Onodera et al. |
| 9,756,697 B2 | 9/2017 | Odnoblyndov et al. |
| 9,761,347 B2 | 9/2017 | Shi et al. |
| 9,761,377 B2 | 9/2017 | Nobuta et al. |
| 9,761,378 B2 | 9/2017 | Shi et al. |
| 9,767,963 B2 | 9/2017 | Uher et al. |
| 9,779,881 B2 | 10/2017 | Ishimaru |
| 9,818,549 B2 | 11/2017 | Chacko |
| 9,875,852 B2 | 1/2018 | Asteman et al. |
| 9,892,859 B2 | 2/2018 | Takatani et al. |
| 9,928,964 B1 | 3/2018 | Jin et al. |
| 9,941,055 B2 | 4/2018 | Chacko et al. |
| 9,953,767 B2 | 4/2018 | Sugihara et al. |
| 9,959,981 B2 | 5/2018 | Merker et al. |
| 9,972,444 B2 | 5/2018 | Petrzilek et al. |
| 9,972,445 B2 | 5/2018 | Koseki et al. |
| 9,991,055 B2 | 6/2018 | Uher et al. |
| 10,014,016 B1 | 7/2018 | Mehfuz et al. |
| 10,026,521 B2 | 7/2018 | Scheel et al. |
| 10,049,822 B2 | 8/2018 | Sugihara et al. |
| 10,062,519 B2 | 8/2018 | Freeman et al. |
| 10,090,111 B2 | 10/2018 | Liu et al. |
| 10,109,421 B2 | 10/2018 | Chacko et al. |
| 10,109,427 B2 | 10/2018 | Ishikawa et al. |
| 10,109,428 B2 | 10/2018 | Shi et al. |
| 10,138,382 B2 | 11/2018 | Lovenich et al. |
| 10,147,551 B2 | 12/2018 | Intelmann et al. |

(56) References Cited

U.S. PATENT DOCUMENTS

| | | |
|---|---|---|
| 10,147,552 B2 | 12/2018 | Takatani et al. |
| 10,208,160 B2 | 2/2019 | Sugihara et al. |
| 10,236,128 B2 | 3/2019 | Tsubaki et al. |
| 10,242,799 B2 | 3/2019 | Chacko et al. |
| 10,249,442 B2 | 4/2019 | Liu et al. |
| 10,283,715 B2 | 5/2019 | Schumann et al. |
| 10,340,091 B2 | 7/2019 | Bunha et al. |
| 10,570,520 B2 | 2/2020 | Jin et al. |
| 10,650,980 B2 | 5/2020 | Bunha et al. |
| 10,658,121 B2 | 5/2020 | Bunha et al. |
| 10,741,333 B2 | 8/2020 | Nakata et al. |
| 10,767,003 B2 | 9/2020 | Scheel et al. |
| 11,139,117 B2 * | 10/2021 | Weaver .................. H01G 9/028 |
| 2002/0021547 A1 | 2/2002 | Sakai et al. |
| 2005/0175861 A1 | 8/2005 | Elschner et al. |
| 2005/0202274 A1 | 9/2005 | Elschner et al. |
| 2007/0064376 A1 * | 3/2007 | Merker .................... H01G 9/04 |
| | | 361/528 |
| 2009/0011226 A1 | 1/2009 | Takeuchi et al. |
| 2009/0035532 A1 | 2/2009 | Bando et al. |
| 2010/0271757 A1 * | 10/2010 | Ishikawa ................ H01G 9/028 |
| | | 361/525 |
| 2011/0019340 A1 | 1/2011 | Nobuto et al. |
| 2011/0026190 A1 | 2/2011 | Oohata |
| 2011/0085285 A1 | 4/2011 | Zednicek et al. |
| 2011/0233450 A1 | 9/2011 | Nobuta et al. |
| 2012/0018662 A1 * | 1/2012 | Sugihara ............. H01G 9/0036 |
| | | 252/62.2 |
| 2012/0075775 A1 * | 3/2012 | Vyroubal ................. H01G 9/15 |
| | | 361/529 |
| 2012/0257325 A1 * | 10/2012 | Zednickova ............. H01G 9/06 |
| | | 361/306.1 |
| 2013/0242464 A1 | 9/2013 | Biler et al. |
| 2013/0273514 A1 | 10/2013 | Tambe et al. |
| 2013/0342967 A1 | 12/2013 | Lai et al. |
| 2014/0022704 A1 | 1/2014 | Petrzilek et al. |
| 2014/0145118 A1 | 5/2014 | Lovenich et al. |
| 2014/0334066 A1 * | 11/2014 | Sugihara ................ H01G 9/028 |
| | | 29/25.03 |
| 2015/0055277 A1 * | 2/2015 | Djebara ................. H01G 9/042 |
| | | 361/528 |
| 2015/0092319 A1 | 4/2015 | Tatsuno et al. |
| 2016/0104580 A1 | 4/2016 | Maeshima et al. |
| 2016/0148757 A1 * | 5/2016 | Djebara ................. H01G 9/145 |
| | | 607/119 |
| 2017/0040116 A1 | 2/2017 | Djebara et al. |
| 2017/0040118 A1 * | 2/2017 | Zednicek ............... H01G 9/012 |
| 2017/0194068 A1 | 7/2017 | Onodera |
| 2017/0207032 A1 * | 7/2017 | Uher ..................... H01G 9/028 |
| 2017/0236647 A1 | 8/2017 | Intelmann et al. |
| 2018/0047988 A1 | 2/2018 | Seuring et al. |
| 2018/0075976 A1 * | 3/2018 | Petrzilek ................ H01G 9/08 |
| 2018/0108487 A1 * | 4/2018 | Petrzilek ............. H01G 9/0032 |
| 2018/0108489 A1 * | 4/2018 | Nakata .................... H01G 9/07 |
| 2018/0244838 A1 | 8/2018 | Miyamoto et al. |
| 2018/0254151 A1 * | 9/2018 | Weaver ................. H01G 9/0425 |
| 2018/0330888 A1 | 11/2018 | Shi et al. |
| 2019/0062501 A1 | 2/2019 | Onodera et al. |
| 2019/0148080 A1 | 5/2019 | Fukui et al. |
| 2019/0311857 A1 | 10/2019 | Bunha et al. |
| 2019/0318879 A1 * | 10/2019 | Weaver ................ H01G 9/0032 |
| 2020/0051750 A1 | 2/2020 | Aoki et al. |
| 2020/0051751 A1 | 2/2020 | Uher et al. |
| 2020/0051757 A1 | 2/2020 | Uher et al. |
| 2020/0118766 A1 | 4/2020 | Miyamoto et al. |
| 2020/0152393 A1 | 5/2020 | Shi et al. |
| 2020/0185157 A1 * | 6/2020 | Uher ........................ H01G 9/08 |

FOREIGN PATENT DOCUMENTS

| | | |
|---|---|---|
| CN | 104409213 | 3/2015 |
| CN | 105405657 A | 3/2016 |
| CN | 105405661 A | 3/2016 |
| CN | 105551801 A | 5/2016 |
| CN | 206040440 U | 3/2017 |
| EP | 0384694 | 8/1990 |
| EP | 1 100 097 B1 | 8/2008 |
| EP | 2 305 686 A1 | 4/2011 |
| EP | 2695904 | 2/2014 |
| EP | 3 318 589 A1 | 5/2018 |
| JP | 2008311582 A | 12/2008 |
| JP | 2010129651 A | 6/2010 |
| JP | 2010153625 A | 7/2010 |
| JP | 2011009499 A | 1/2011 |
| JP | 2011009568 A | 1/2011 |
| JP | 2011009569 A | 1/2011 |
| JP | 2011114208 A | 6/2011 |
| JP | 2011135020 A | 7/2011 |
| JP | 2011195764 A | 10/2011 |
| JP | 2011199086 A | 10/2011 |
| JP | 2011199087 A | 10/2011 |
| JP | 2011199088 A | 10/2011 |
| JP | 2011216752 A | 10/2011 |
| JP | 2011253878 A | 12/2011 |
| JP | 2012015425 A | 1/2012 |
| JP | 2012025887 A | 2/2012 |
| JP | 2012049432 A | 3/2012 |
| JP | 2012174948 A | 9/2012 |
| JP | 2012188400 A | 10/2012 |
| JP | 2012191127 A | 10/2012 |
| JP | 2012199364 A | 10/2012 |
| JP | 2012244077 A | 12/2012 |
| JP | 2013006969 A | 1/2013 |
| JP | 2013055308 A | 3/2013 |
| JP | 2013074212 A | 4/2013 |
| JP | 2013116939 A | 6/2013 |
| JP | 2013127045 A | 6/2013 |
| JP | 2013163793 A | 8/2013 |
| JP | 2013251359 A | 12/2013 |
| JP | 2013251408 A | 12/2013 |
| JP | 2014003322 A | 1/2014 |
| JP | 2014007401 A | 1/2014 |
| JP | 2014011218 A | 1/2014 |
| JP | 2014011222 A | 1/2014 |
| JP | 2014024905 A | 2/2014 |
| JP | 2014027040 A | 2/2014 |
| JP | 2014041888 A | 3/2014 |
| JP | 2014043500 A | 3/2014 |
| JP | 2014060231 A | 4/2014 |
| JP | 2014093417 A | 5/2014 |
| JP | 2014135525 A | 7/2014 |
| JP | 2014198827 A | 10/2014 |
| JP | 2014201545 A | 10/2014 |
| JP | 5637544 B2 | 12/2014 |
| JP | 5663871 B2 | 2/2015 |
| JP | 2015021100 A | 2/2015 |
| JP | 2015095616 A | 5/2015 |
| JP | 2015105315 A | 6/2015 |
| JP | 2015118978 A | 6/2015 |
| JP | 5745881 B2 | 7/2015 |
| JP | 2015165550 A | 9/2015 |
| JP | 5807997 B2 | 11/2015 |
| JP | 2016009770 A | 1/2016 |
| JP | 5892535 B2 | 3/2016 |
| JP | 5911136 B2 | 4/2016 |
| JP | 5954798 B2 | 7/2016 |
| JP | 2016135839 A | 7/2016 |
| JP | 5988824 B2 | 9/2016 |
| JP | 5988831 B2 | 9/2016 |
| JP | 5998836 B2 | 9/2016 |
| JP | 6015243 B2 | 10/2016 |
| JP | 6015244 B2 | 10/2016 |
| JP | 6024264 B2 | 11/2016 |
| JP | 2016188348 A | 11/2016 |
| JP | 6096727 B2 | 3/2017 |
| JP | 2017045868 A | 3/2017 |
| JP | 2017048291 A | 3/2017 |
| JP | 2017057267 A | 3/2017 |
| JP | 2017095589 A | 6/2017 |
| JP | 2017101102 A | 6/2017 |
| JP | 6180010 B2 | 8/2017 |
| JP | 2017141409 A | 8/2017 |
| JP | 6201595 B2 | 9/2017 |

(56) References Cited

FOREIGN PATENT DOCUMENTS

| | | | |
|---|---|---|---|
| JP | 2017171759 A | 9/2017 | |
| JP | 2017188640 A | 10/2017 | |
| JP | 6256970 B2 | 1/2018 | |
| JP | 6273917 B2 | 2/2018 | |
| JP | 6311355 B2 | 4/2018 | |
| JP | 2018090755 A | 6/2018 | |
| JP | 6379523 B2 | 8/2018 | |
| JP | 2018123213 A | 8/2018 | |
| JP | 6415146 B2 | 10/2018 | |
| JP | 6427887 B2 | 11/2018 | |
| JP | 2018184586 A | 11/2018 | |
| JP | 2018193513 A | 12/2018 | |
| JP | 2018204029 A | 12/2018 | |
| JP | 64622.55 B2 | 1/2019 | |
| JP | 6485074 B2 | 3/2019 | |
| WO | WO 2006/088033 A1 | 8/2006 | |
| WO | WO 2008/036909 A2 | 3/2008 | |
| WO | WO 2010/095650 A1 | 8/2010 | |
| WO | WO 2010/095651 A1 | 8/2010 | |
| WO | WO 2010/095652 A1 | 8/2010 | |
| WO | WO 2012/014844 A1 | 2/2012 | |
| WO | WO 2015119047 A1 | 8/2015 | |
| WO | WO 2016/111277 A1 | 7/2016 | |
| WO | WO 2018/097085 A1 | 5/2018 | |
| WO | WO 2019/026961 A1 | 2/2019 | |

OTHER PUBLICATIONS

U.S. Appl. No. 10/475,591, filed Nov. 2019, Vile et al.

Merker et al., "New Conducting Polymer Dispersions for Solid Electrolyte Capacitors," *CARTS Europe 2005 (Prague, Czech Republic)*, Oct. 17-20, 2005, 6 pages.

Merker et al., "Conducting Polymer Dispersions for High-Capacitance Tantalum Capacitors," *CARTS Europe 2006*, 6 pages.

Safety Data Sheet for Selftron® S (Prototype) from Tosoh Corporation, Nov. 1, 2016, 9 pages.

Product Information on Self-doped Conductive Polymer TS-CP90 from Tosoh Corporation, 1 page.

Simpson et al., "Advances and Applications of Inherently Conductive Polymer Technologies Based on Poly(3,4-Ethylenedioxythiophene)," *2005 AIMCAL Fall Technical Conference and 19$^{th}$ International Vacuum Web Coating Conference* (Myrtle Beach, SC), Oct. 16-20, 2005, Session 5: Advances in Technology, 10 pages.

Ye et al., "Freestanding flexible polymer films based on bridging of two EDOT units with functionalized chains for use in long-term-stable capacitors," *New J. Chem.*, 2018, 42, pp. 4824-4834.

International Search Report for PCT/US2020/051459 dated Dec. 13, 2020, 13 pages.

* cited by examiner

SOLID ELECTROLYTIC CAPACITOR FOR USE AT HIGH VOLTAGES

CROSS REFERENCE TO RELATED APPLICATION

The present application claims filing benefit of U.S. Provisional Patent Application Ser. No. 62/901,915 having a filing date of Sep. 18, 2019, which is incorporated herein by reference in its entirety.

BACKGROUND OF THE INVENTION

Solid electrolytic capacitors (e.g., tantalum capacitors) are typically made by pressing a metal powder (e.g., tantalum) around a metal lead wire, sintering the pressed part, anodizing the sintered anode, and thereafter applying a solid electrolyte. Intrinsically conductive polymers are often employed as the solid electrolyte due to their advantageous low equivalent series resistance ("ESR") and "non-burning/non-ignition" failure mode. Such electrolytes can be formed through in situ polymerization of the monomer in the presence of a catalyst and dopant. Alternatively, premade conductive polymer slurries may also be employed. Regardless of how they are formed, one problem with conductive polymer electrolytes is that they are inherently weak, which can sometimes cause them to delaminate from the dielectric during formation of the capacitor or during its operation. Furthermore, in high voltage applications, the quality of the dielectric layer may cause failure of the part. For example, high voltage power distribution systems deliver a high voltage to the capacitor that can result in an inrush or "surge" current, particularly during a fast switch on or during an operational current spike. The peak surge current that the capacitor can withstand without failure may be in part related to the quality of the dielectric. Because the thinner areas have a lower resistance than the thicker neighboring areas, the power dissipated in the thinner areas is generally greater. Therefore, when a surge current is applied, these thinner areas may develop into weak "hot spots" that ultimately lead to degradation and breakdown of the dielectric.

As such, a need currently exists for a solid electrolytic capacitor having improved performance in high voltage environments.

SUMMARY OF THE INVENTION

In accordance with one embodiment of the present invention, a capacitor is disclosed that comprises a capacitor element. The capacitor element comprises a sintered porous anode body, a dielectric that overlies the anode body, and a solid electrolyte that overlies the dielectric. The solid electrolyte contains an inner layer and an outer layer, wherein the inner layer is formed from an in situ-polymerized conductive polymer and the outer layer is formed from pre-polymerized conductive polymer particles. Further, the in-situ polymerized conductive polymer is formed from an alkylated thiophene monomer having the following general structure:

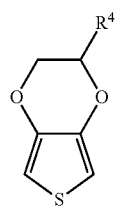

wherein, $R^4$ is an alkyl group.

Other features and aspects of the present invention are set forth in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

DETAILED DESCRIPTION OF REPRESENTATIVE EMBODIMENTS

Figure 1:
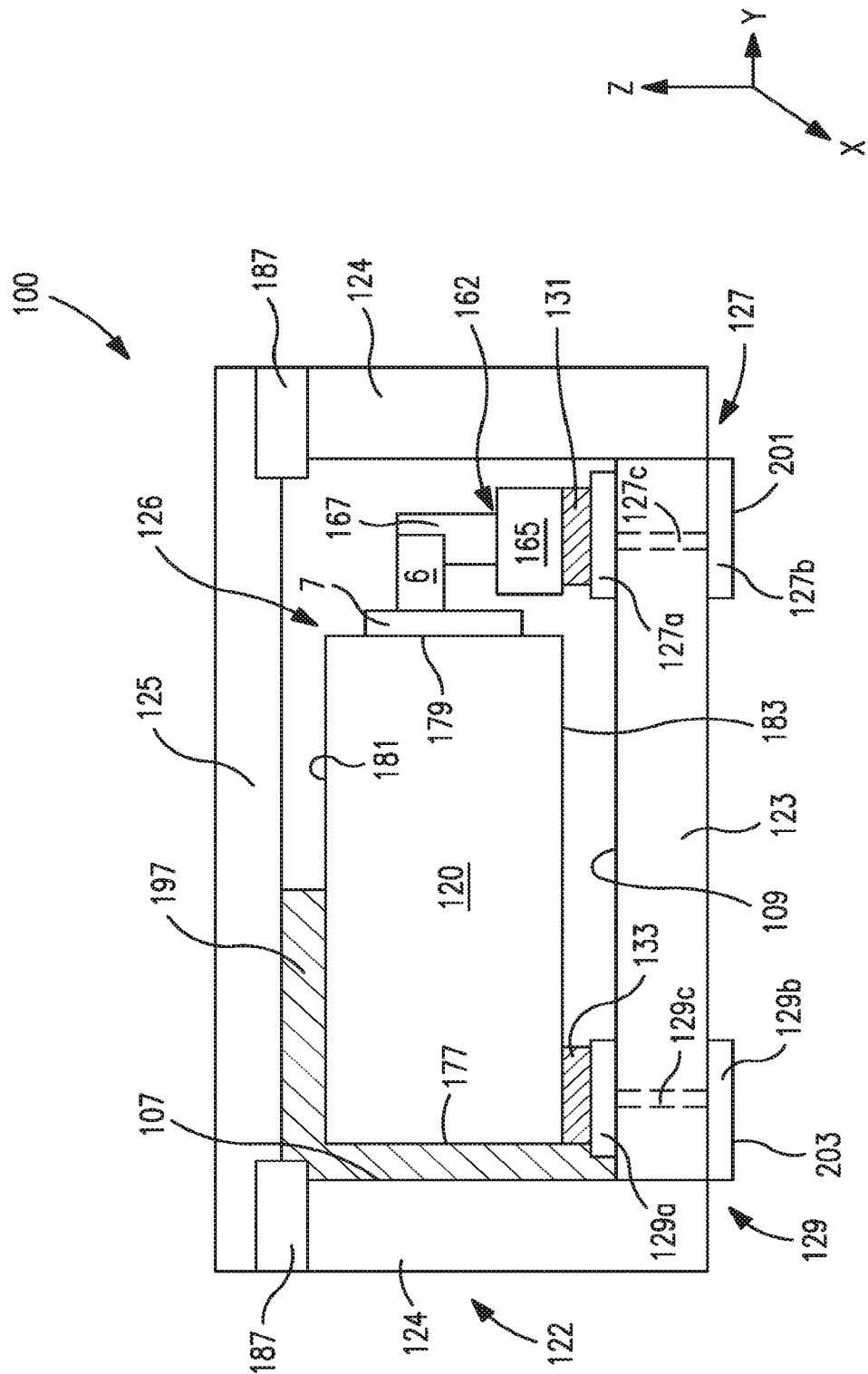
FIG. 1 is a cross-sectional view of one embodiment of a capacitor of the assembly of the present invention.

It is to be understood by one of ordinary skill in the art that the present discussion is a description of exemplary embodiments only, and is not intended as limiting the broader aspects of the present invention, which broader aspects are embodied in the exemplary construction.

Generally speaking, the present invention is directed to a capacitor that is capable of exhibiting good electrical properties under a wide variety of different conditions. More particularly, the capacitor contains a capacitor element that includes a sintered porous anode body and a dielectric that overlies the anode body. A solid electrolyte overlies the dielectric that contains an inner layer formed from an in situ-polymerized conductive polymer that is derived from an alkylated thiophene monomer and an outer layer formed from pre-polymerized conductive polymer particles.

The present inventors have discovered that the combination of the specific types of inner solid electrolyte layer and outer solid electrolyte layer can result in a capacitor having a unique and beneficial array of properties, even when exposed to high voltage environments. For example, the capacitor can be formed with a high degree of dielectric strength, which can improve capacitance stability. The "dielectric strength" generally refers to the ratio of the "breakdown voltage" of the capacitor (voltage at which the capacitor fails in volts, "V") to the thickness of the dielectric (in nanometers, "nm"). The capacitor typically exhibits a dielectric strength of about 0.5 V/nm or more, in some embodiments about 0.52 V/nm or more, in some embodiments about 0.55 V/nm or more, in some embodiments about 0.56 or more, and in some embodiments, from about 0.59 to about 0.9 V/nm. The capacitor may, for example, exhibit a relatively high "breakdown voltage" (voltage at which the capacitor fails), such as about 25 volts or more, in some embodiments about 27 volts or more, in some embodiments about 28 volts or more, in some embodiments about 29 volts or more, and in some embodiments, from about 30 volts to about 100 volts. While its thickness can generally vary depending on the particular location of the anode body, the "dielectric thickness" typically ranges from about 40 to about 100 nm, in some embodiments from about 45 to about 90 nm, and in some embodiments, from about 50 to about 85 nm.

The capacitor may also exhibit a relatively low equivalence series resistance ("ESR"), such as about 200 mohms, in some embodiments less than about 150 mohms, in some embodiments from about 0.1 to about 125 mohms, and in some embodiments, from about 1 to about 100 mohms, measured at an operating frequency of 100 kHz and temperature of 23° C. The capacitor may also exhibit a dry capacitance of about 30 nanoFarads per square centimeter ("nF/cm$^2$") or more, in some embodiments about 100 nF/cm$^2$ or more, in some embodiments from about 200 to about 3,000 nF/cm$^2$, and in some embodiments, from about 400 to about 2,000 nF/cm$^2$, measured at a frequency of 120 Hz at temperature of 23° C. In addition, the capacitor may also exhibit a leakage current ("DCL") of only about 30 microamps ("μA") or less, in some embodiments about 25 μA or less, in some embodiments about 20 μA or less, in some embodiments about 5 μA or less, in some embodiments about 3.5 μA or less, and in some embodiments, from about 0.1 to about 3 μA as determined at a temperature of 23° C.

Notably, such electrical properties (e.g., ESR, capacitance, and/or DCL) can still remain stable even at high temperatures. For example, the capacitor may exhibit ESR, capacitance, or DCL values within the ranges noted above even after being exposed to a temperature of from about 80° C. or more, in some embodiments from about 100° C. to about 200° C., and in some embodiments, from about 105° C. to about 180° C. (e.g., 85° C., 105° C., 125° C., or 150° C.). In one embodiment, for example, the ratio of the ESR and/or capacitance value of the capacitor after being exposed to the high temperature (e.g., 125° C.) to the initial ESR and/or capacitance value of the capacitor (e.g., at 23° C.) is about 0.5 or more, in some embodiments about 0.7 or more, in some embodiments from about 0.8 to 1, and in some embodiments, from about 0.9 to 1. Likewise, the ratio of the DCL of the capacitor after being exposed to a high temperature (e.g., 125° C.) to the initial DCL value of the capacitor (e.g., at 23° C.) is about 10 or less, in some embodiments about 8 or less, in some embodiments from about 0.5 to about 7, and in some embodiments, from about 0.8 to about 6.

The capacitor may also exhibit ESR, capacitance, or DCL values within the ranges noted above after being exposed to a high relative humidity level, either at room temperature (23° C.) or a high temperature as noted above (e.g., 85° C., 125° C., or 150° C.). Such high relative humidity levels may, for instance, be about 40% or more, in some embodiments about 45% or more, in some embodiments about 50% or more, and in some embodiments, about 70% or more (e.g., about 85% to 100%) for a substantial period of time as noted above. Relative humidity may, for instance, be determined in accordance with ASTM E337-02, Method A (2007). In one embodiment, for example, the ratio of the DCL value of the capacitor after being exposed to high humidity (e.g., 85%) to the initial DCL value of the capacitor is about 10 or less, in some embodiments about 8 or less, in some embodiments from about 0.5 to about 7, and in some embodiments, from about 0.8 to about 6.

Various embodiments of the invention will now be described in more detail.

I. Capacitor Element

A. Anode Body

The capacitor element includes an anode that contains a dielectric formed on a sintered porous body. The porous anode body may be formed from a powder that contains a valve metal (i.e., metal that is capable of oxidation) or valve metal-based compound, such as tantalum, niobium, aluminum, hafnium, titanium, alloys thereof, oxides thereof, nitrides thereof, and so forth. The powder is typically formed from a reduction process in which a tantalum salt (e.g., potassium fluotantalate ($K_2TaF_7$), sodium fluotantalate ($Na_2TaF_7$), tantalum pentachloride ($TaCl_5$), etc.) is reacted with a reducing agent. The reducing agent may be provided in the form of a liquid, gas (e.g., hydrogen), or solid, such as a metal (e.g., sodium), metal alloy, or metal salt. In one embodiment, for instance, a tantalum salt (e.g., $TaCl_5$) may be heated at a temperature of from about 900° C. to about 2,000° C., in some embodiments from about 1,000° C. to about 1,800° C., and in some embodiments, from about 1,100° C. to about 1,600° C., to form a vapor that can be reduced in the presence of a gaseous reducing agent (e.g., hydrogen). Additional details of such a reduction reaction may be described in WO 2014/199480 to Maeshima, et al. After the reduction, the product may be cooled, crushed, and washed to form a powder.

The specific charge of the powder typically varies from about 2,000 to about 800,000 microFarads*Volts per gram ("μF*V/g") depending on the desired application. For instance, in certain embodiments, a high charge powder may be employed that has a specific charge of from about 100,000 to about 800,000 μF*V/g, in some embodiments from about 120,000 to about 700,000 μF*V/g, and in some embodiments, from about 150,000 to about 600,000 μF*V/g. In other embodiments, a low charge powder may be employed that has a specific charge of from about 2,000 to about 100,000 μF*V/g, in some embodiments from about 5,000 to about 80,000 μF*V/g, and in some embodiments, from about 10,000 to about 70,000 μF*V/g. As is known in the art, the specific charge may be determined by multiplying capacitance by the anodizing voltage employed, and then dividing this product by the weight of the anodized electrode body.

The powder may be a free-flowing, finely divided powder that contains primary particles. The primary particles of the powder generally have a median size (D50) of from about 5 to about 250 nanometers, in some embodiments from about 10 to about 200 nanometers, and in some embodiments, from about 20 to about 150 nanometers, such as determined using a laser particle size distribution analyzer made by BECKMAN COULTER Corporation (e.g., LS-230), optionally after subjecting the particles to an ultrasonic wave vibration of 70 seconds. The primary particles typically have a three-dimensional granular shape (e.g., nodular or angular). Such particles typically have a relatively low "aspect ratio", which is the average diameter or width of the particles divided by the average thickness ("D/T"). For example, the aspect ratio of the particles may be about 4 or less, in some embodiments about 3 or less, and in some embodiments, from about 1 to about 2. In addition to primary particles, the powder may also contain other types of particles, such as secondary particles formed by aggregating (or agglomerating) the primary particles. Such secondary particles may have a median size (D50) of from about 1 to about 500 micrometers, and in some embodiments, from about 10 to about 250 micrometers.

Agglomeration of the particles may occur by heating the particles and/or through the use of a binder. For example, agglomeration may occur at a temperature of from about 0° C. to about 40° C., in some embodiments from about 5° C. to about 35° C., and in some embodiments, from about 15° C. to about 30° C. Suitable binders may likewise include, for instance, poly(vinyl butyral); poly(vinyl acetate); poly(vinyl alcohol); poly(vinyl pyrollidone); cellulosic polymers, such as carboxymethylcellulose, methyl cellulose, ethyl cellulose, hydroxyethyl cellulose, and methylhydroxyethyl cellulose; atactic polypropylene, polyethylene; polyethylene glycol (e.g., Carbowax from Dow Chemical Co.); polystyrene, poly(butadiene/styrene); polyamides, polyimides, and polyacrylamides, high molecular weight polyethers; copolymers of ethylene oxide and propylene oxide; fluoropolymers, such as polytetrafluoroethylene, polyvinylidene fluoride, and fluoro-olefin copolymers; acrylic polymers, such as sodium polyacrylate, poly(lower alkyl acrylates), poly (lower alkyl methacrylates) and copolymers of lower alkyl acrylates and methacrylates; and fatty acids and waxes, such as stearic and other soapy fatty acids, vegetable wax, microwaxes (purified paraffins), etc.

The resulting powder may be compacted to form a pellet using any conventional powder press device. For example, a press mold may be employed that is a single station compaction press containing a die and one or multiple punches. Alternatively, anvil-type compaction press molds may be used that use only a die and single lower punch. Single station compaction press molds are available in several basic types, such as cam, toggle/knuckle and eccentric/crank presses with varying capabilities, such as single action, double action, floating die, movable platen, opposed ram, screw, impact, hot pressing, coining or sizing. The powder may be compacted around an anode lead, which may be in the form of a wire, sheet, etc. The lead may extend in a longitudinal direction from the anode body and may be formed from any electrically conductive material, such as tantalum, niobium, aluminum, hafnium, titanium, etc., as well as electrically conductive oxides and/or nitrides of thereof. Connection of the lead may also be accomplished using other known techniques, such as by welding the lead to the body or embedding it within the anode body during formation (e.g., prior to compaction and/or sintering).

Any binder may be removed after pressing by heating the pellet under vacuum at a certain temperature (e.g., from about 150° C. to about 500° C.) for several minutes. Alternatively, the binder may also be removed by contacting the pellet with an aqueous solution, such as described in U.S. Pat. No. 6,197,252 to Bishop, et al. Thereafter, the pellet is sintered to form a porous, integral mass. The pellet is typically sintered at a temperature of from about 700° C. to about 1600° C., in some embodiments from about 800° C. to about 1500° C., and in some embodiments, from about 900° C. to about 1200° C., for a time of from about 5 minutes to about 100 minutes, and in some embodiments, from about 8 minutes to about 15 minutes. This may occur in one or more steps. If desired, sintering may occur in an atmosphere that limits the transfer of oxygen atoms to the anode. For example, sintering may occur in a reducing atmosphere, such as in a vacuum, inert gas, hydrogen, etc. The reducing atmosphere may be at a pressure of from about 10 Torr to about 2000 Torr, in some embodiments from about 100 Torr to about 1000 Torr, and in some embodiments, from about 100 Torr to about 930 Torr. Mixtures of hydrogen and other gases (e.g., argon or nitrogen) may also be employed.

B. Dielectric

The anode is also coated with a dielectric. The dielectric may be formed by anodically oxidizing ("anodizing") the sintered anode so that a dielectric layer is formed over and/or within the anode. For example, a tantalum (Ta) anode may be anodized to tantalum pentoxide ($Ta_2O_5$). Typically, anodization is performed by initially applying a solution to the anode, such as by dipping anode into the electrolyte. A solvent is generally employed, such as water (e.g., deionized water). To enhance ionic conductivity, a compound may be employed that is capable of dissociating in the solvent to form ions. Examples of such compounds include, for instance, acids, such as described below with respect to the electrolyte. For example, an acid (e.g., phosphoric acid) may constitute from about 0.01 wt. % to about 5 wt. %, in some embodiments from about 0.05 wt. % to about 0.8 wt. %, and in some embodiments, from about 0.1 wt. % to about 0.5 wt. % of the anodizing solution. If desired, blends of acids may also be employed.

A current is passed through the anodizing solution to form the dielectric layer. The value of the formation voltage manages the thickness of the dielectric layer. For example, the power supply may be initially set up at a galvanostatic mode until the required voltage is reached. Thereafter, the power supply may be switched to a potentiostatic mode to ensure that the desired dielectric thickness is formed over the entire surface of the anode. Of course, other known methods may also be employed, such as pulse or step potentiostatic methods. The voltage at which anodic oxidation occurs typically ranges from about 4 to about 250 V, and in some embodiments, from about 9 to about 200 V, and in some embodiments, from about 20 to about 150 V. During oxidation, the anodizing solution can be kept at an elevated temperature, such as about 30° C. or more, in some embodiments from about 40° C. to about 200° C., and in some embodiments, from about 50° C. to about 100° C. Anodic oxidation can also be done at ambient temperature or lower. The resulting dielectric layer may be formed on a surface of the anode and within its pores.

Figure 5:
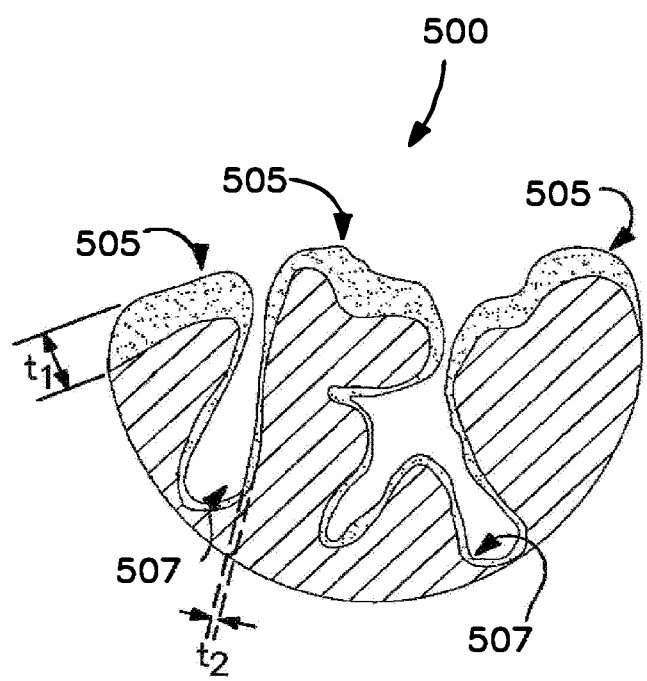
FIG. 5 is a schematic illustration of a dielectric layer with a differential thickness in accordance with one embodiment of the present invention.

Although not required, in certain embodiments, the dielectric layer may possess a differential thickness throughout the anode in that it possesses a first portion that overlies an external surface of the anode and a second portion that overlies an interior surface of the anode. In such embodiments, the first portion is selectively formed so that its thickness is greater than that of the second portion. It should be understood, however, that the thickness of the dielectric layer need not be uniform within a particular region. Certain portions of the dielectric layer adjacent to the external surface may, for example, actually be thinner than certain portions of the layer at the interior surface, and vice versa. Nevertheless, the dielectric layer may be formed such that at least a portion of the layer at the external surface has a greater thickness than at least a portion at the interior surface. FIG. 5, for instance, shows one embodiment in which an anode body 500 contains a dielectric layer having a first external portion 505 with a thickness "t1" and a second internal portion 507 with a thickness "t2", wherein the thickness "t1" is greater than the thickness "t2." Although the exact difference in these thicknesses may vary depending on the particular application, the ratio of the thickness of the first portion to the thickness of the second portion is typically from about 1.2 to about 40, in some embodiments from about 1.5 to about 25, and in some embodiments, from about 2 to about 20.

To form a dielectric layer having a differential thickness, a multi-stage process is generally employed. In each stage of the process, the sintered anode is anodically oxidized ("anodized") to form a dielectric layer (e.g., tantalum pentoxide). During the first stage of anodization, a relatively small forming voltage is typically employed to ensure that the desired dielectric thickness is achieved for the inner region, such as forming voltages ranging from about 1 to about 90 volts, in some embodiments from about 2 to about 50 volts, and in some embodiments, from about 5 to about 20 volts. Thereafter, the sintered body may then be anodically oxidized in a second stage of the process to increase the thickness of the dielectric to the desired level. This is generally accomplished by anodizing in an electrolyte at a higher voltage than employed during the first stage, such as at forming voltages ranging from about 50 to about 350 volts, in some embodiments from about 60 to about 300 volts, and in some embodiments, from about 70 to about 200 volts. During the first and/or second stages, the electrolyte may be kept at a temperature within the range of from about 15° C. to about 95° C., in some embodiments from about 20° C. to about 90° C., and in some embodiments, from about 25° C. to about 85° C.

The electrolytes employed during the first and second stages of the anodization process may be the same or different. Typically, however, it is desired to employ different solutions to help better facilitate the attainment of a higher thickness at the outer portions of the dielectric layer. For example, it may be desired that the electrolyte employed in the second stage has a lower ionic conductivity than the electrolyte employed in the first stage to prevent a significant amount of oxide film from forming on the internal surface of anode. In this regard, the electrolyte employed during the first stage may contain an acidic compound, such as hydrochloric acid, nitric acid, sulfuric acid, phosphoric acid, polyphosphoric acid, boric acid, boronic acid, etc. Such an electrolyte may have an electrical conductivity of from about 0.1 to about 100 mS/cm, in some embodiments from about 0.2 to about 20 mS/cm, and in some embodiments, from about 1 to about 10 mS/cm, determined at a temperature of 25° C. The electrolyte employed during the second stage typically contains a salt of a weak acid so that the hydronium ion concentration increases in the pores as a result of charge passage therein. Ion transport or diffusion is such that the weak acid anion moves into the pores as necessary to balance the electrical charges. As a result, the concentration of the principal conducting species (hydronium ion) is reduced in the establishment of equilibrium between the hydronium ion, acid anion, and undissociated acid, thus forms a poorer-conducting species. The reduction in the concentration of the conducting species results in a relatively high voltage drop in the electrolyte, which hinders further anodization in the interior while a thicker oxide layer, is being built up on the outside to a higher formation voltage in the region of continued high conductivity. Suitable weak acid salts may include, for instance, ammonium or alkali metal salts (e.g., sodium, potassium, etc.) of boric acid, boronic acid, acetic acid, oxalic acid, lactic acid, adipic acid, etc. Particularly suitable salts include sodium tetraborate and ammonium pentaborate. Such electrolytes typically have an electrical conductivity of from about 0.1 to about 20 mS/cm, in some embodiments from about 0.5 to about 10 mS/cm, and in some embodiments, from about 1 to about 5 mS/cm, determined at a temperature of 25° C.

If desired, each stage of anodization may be repeated for one or more cycles to achieve the desired dielectric thickness. Furthermore, the anode may also be rinsed or washed with another solvent (e.g., water) after the first and/or second stages to remove the electrolyte.

C. Solid Electrolyte

A solid electrolyte overlies the dielectric and generally functions as the cathode for the capacitor. The solid electrolyte contains one or more inner layers and one or more outer layers that overly the inner layer(s). The term "inner" in this context refers to one or more layers that overly the dielectric, whether directly or via another layer (e.g., precoat layer). Likewise, the term "outer" refers to one or more layers that overly the inner layer(s) and that may be formed from a different material.

i. Inner Layer

As indicated above, the solid electrolyte typically contains one or more "inner" layers that contain a conductive polymer that is in situ-polymerized. For example, such in situ-polymerized conductive polymers may constitute about 50 wt. % or more, in some embodiments about 70 wt. % or more, and in some embodiments, about 90 wt. % or more (e.g., 100 wt. %) of the inner layer(s). One or multiple inner layers may be employed. For example, the solid electrolyte may contain from 2 to 30, in some embodiments from 4 to 20, and in some embodiments, from about 5 to 15 inner layers (e.g., 10 layers). Regardless, the conductive polymer of the inner layer(s) may be formed from an alkylated thiophene monomer having the following general structure:

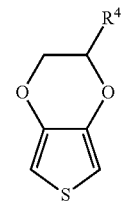

wherein, $R^4$ is an alkyl group (e.g., methyl, ethyl, propyl, butyl, etc.).

When $R^4$ is a methyl group, the resulting compound may be referred to as 2-methyl-2,3-dihydro-thieno[3,4-b][1,4]dioxine ("methylated ethylenedioxythiophene"). When $R^4$ is an ethyl group, the resulting compound may be referred to as 2-ethyl-2,3-dihydro-thieno[3,4-b][1,4]dioxine ("ethylated ethylenedioxythiophene"). When $R^4$ is a propyl group, the resulting compound may be referred to as 2-propyl-2,3-dihydro-thieno[3,4-b][1,4]dioxine ("propylated ethylenedioxythiophene"). Finally, when $R^4$ is a butyl group, the resulting compound may be referred to as 2-butyl-2,3-dihydro-thieno[3,4-b][1,4]dioxine ("butylated ethylenedioxythiophene"). In certain embodiments, it may be desirable to use a combination of monomers, such as an alkylated thiophene derivative in combination with a non-alkylated thiophene derivative (e.g., 3,4-ethylenedioxythiophene). In such embodiments, the weight ratio of the alkylated monomer to the non-alkylated monomer may range from about 0.1:1 to about 1:0.1, in some embodiments from about 0.2:1 to about 1:0.2, and in some embodiments, from about 0.3:1 to 1:0.3.

To form an in situ-polymerized layer, the precursor monomer may be polymerized in the presence of an oxidative catalyst (e.g., chemically polymerized). The oxidative catalyst typically includes a transition metal cation, such as iron(III), copper(II), chromium(VI), cerium(IV), manganese (IV), manganese(VII), or ruthenium(III) cations, and etc. A dopant may also be employed to provide excess charge to the conductive polymer and stabilize the conductivity of the polymer. The dopant typically includes an inorganic or organic anion, such as an ion of a sulfonic acid. In certain embodiments, the oxidative catalyst has both a catalytic and doping functionality in that it includes a cation (e.g., transition metal) and an anion (e.g., sulfonic acid). For example, the oxidative catalyst may be a transition metal salt that includes iron(III) cations, such as iron(III) halides (e.g., $FeCl_3$) or iron(III) salts of other inorganic acids, such as $Fe(ClO_4)_3$ or $Fe_2(SO_4)_3$ and the iron(III) salts of organic acids and inorganic acids comprising organic radicals. Examples of iron (III) salts of inorganic acids with organic radicals include, for instance, iron(III) salts of sulfuric acid monoesters of $C_1$ to $C_{20}$ alkanols (e.g., iron(III) salt of lauryl sulfate). Likewise, examples of iron(III) salts of organic acids include, for instance, iron(III) salts of $C_1$ to $C_{20}$ alkane sulfonic acids (e.g., methane, ethane, propane, butane, or dodecane sulfonic acid); iron (III) salts of aliphatic perfluorosulfonic acids (e.g., trifluoromethane sulfonic acid, perfluorobutane sulfonic acid, or perfluorooctane sulfonic acid); iron (III) salts of aliphatic $C_1$ to $C_{20}$ carboxylic acids (e.g., 2-ethylhexylcarboxylic acid); iron (III) salts of aliphatic perfluorocarboxylic acids (e.g., trifluoroacetic acid or perfluorooctane acid); iron (III) salts of aromatic sulfonic acids optionally substituted by $C_1$ to $C_{20}$ alkyl groups (e.g., benzene sulfonic acid, o-toluene sulfonic acid, p-toluene sulfonic acid, or dodecylbenzene sulfonic acid); iron (III) salts of cycloalkane sulfonic acids (e.g., camphor sulfonic acid); and so forth. Mixtures of these above-mentioned iron(III) salts may also be used. Iron(III)-p-toluene sulfonate, iron(III)-o-toluene sulfonate, and mixtures thereof, are particularly suitable. One commercially suitable example of iron(III)-p-toluene sulfonate is available from Heraeus under the designation Clevios™ C.

The oxidative catalyst and precursor monomer may be applied either sequentially or together to initiate the polymerization reaction. Suitable application techniques for applying these components include screen-printing, dipping, electrophoretic coating, and spraying. As an example, the monomer may initially be mixed with the oxidative catalyst to form a precursor solution. Once the mixture is formed, it may be applied to the anode and then allowed to polymerize so that a conductive coating is formed on the surface. Alternatively, the oxidative catalyst and monomer may be applied sequentially. In one embodiment, for example, the oxidative catalyst is dissolved in an organic solvent (e.g., butanol) and then applied as a dipping solution. The part may then be dried to remove the solvent therefrom. Thereafter, the part may be dipped into a solution containing the monomer. Regardless, polymerization is typically performed at temperatures of from about −10° C. to about 250° C., and in some embodiments, from about 0° C. to about 200° C., depending on the oxidizing agent used and desired reaction time. Suitable polymerization techniques, such as described above, may be described in more detail in U.S. Pat. No. 7,515,396 to Biler. Still other methods for applying such conductive coating(s) may be described in U.S. Pat. No. 5,457,862 to Sakata, et al., U.S. Pat. No. 5,473,503 to Sakata, et al., U.S. Pat. No. 5,729,428 to Sakata, et al., and U.S. Pat. No. 5,812,367 to Kudoh, et al.

ii. Outer Layer

As noted above, the solid electrolyte also contains one or more "outer" layers that may be formed from a different material than the inner layer(s) and overly the inner layer(s). More particularly, the outer layer(s) may be formed from pre-polymerized intrinsically and/or extrinsically conductive polymer particles. One benefit of employing such particles is that they can minimize the presence of ionic species (e.g., $Fe^{2+}$ or $Fe^{3+}$) produced during conventional in situ polymerization processes, which can cause dielectric breakdown under high electric field due to ionic migration. Thus, by applying the conductive polymer as pre-polymerized particles rather through in situ polymerization, the resulting capacitor may exhibit an even high breakdown voltage. In one particular embodiment, for example, the outer layer(s) are formed primarily from such conductive polymer particles in that they constitute about 50 wt. % or more, in some embodiments about 70 wt. % or more, and in some embodiments, about 90 wt. % or more (e.g., 100 wt. %) of a respective outer layer. One or multiple outer layers may be employed. For example, the solid electrolyte may contain from 2 to 30, in some embodiments from 3 to 25, and in some embodiments, from about 4 to 20 outer layers, each of which may optionally be formed from a dispersion of the pre-polymerized conductive polymer particles. Regardless of the number of layers employed, the resulting solid electrolyte, including all of the inner layer(s) and outer layer(s), typically has a total a thickness of from about 1 micrometer (μm) to about 200 μm, in some embodiments from about 2 μm to about 50 μm, and in some embodiments, from about 3 μm to about 30 μm.

As indicated above, the conductive polymer particles of the outer layer(s) may be formed from an extrinsically and/or intrinsically conductive polymer. In certain embodiments, an "extrinsically" conductive polymer may be employed in the solid electrolyte that has repeating units of the repeating units of the following formula (I):

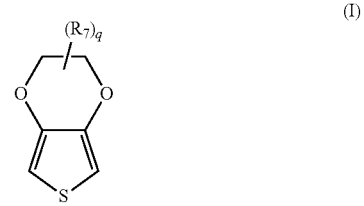

wherein, $R_7$ is a linear or branched, $C_1$ to $C_{18}$ alkyl radical (e.g., methyl, ethyl, n- or iso-propyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadecyl, n-octadecyl, etc.); $C_5$ to $C_{12}$ cycloalkyl radical (e.g., cyclopentyl, cyclohexyl, cycloheptyl, cyclooctyl, cyclononyl, cyclodecyl, etc.); $C_6$ to $C_{14}$ aryl radical (e.g., phenyl, naphthyl, etc.); $C_7$ to $C_{18}$ aralkyl radical (e.g., benzyl, o-, m-, p-tolyl, 2,3-, 2,4-, 2,5-, 2-6, 3-4-, 3,5-xylyl, mesityl, etc.); and q is an integer from 0 to 8, in some embodiments, from 0 to 2, and in one embodiment, 0. In one particular embodiment, "q" is 0 and the polymer is poly(3,4-ethylenedioxythiophene). One commercially suitable example of a monomer suitable for forming such a polymer is 3,4-ethylenedioxthiophene, which is available from Heraeus under the designation Clevios™ M.

The polymers of formula (I) are generally considered to be "extrinsically" conductive to the extent that they typically require the presence of a separate counterion that is not covalently bound to the polymer. The counterion may be a monomeric or polymeric anion that counteracts the charge of the conductive polymer. Polymeric anions can, for example, be anions of polymeric carboxylic acids (e.g., polyacrylic acids, polymethacrylic acid, polymaleic acids, etc.); polymeric sulfonic acids (e.g., polystyrene sulfonic acids ("PSS"), polyvinyl sulfonic acids, etc.); and so forth. The acids may also be copolymers, such as copolymers of vinyl carboxylic and vinyl sulfonic acids with other polymerizable monomers, such as acrylic acid esters and styrene. Likewise, suitable monomeric anions include, for example, anions of $C_1$ to $C_{20}$ alkane sulfonic acids (e.g., dodecane sulfonic acid); aliphatic perfluorosulfonic acids (e.g., trifluoromethane sulfonic acid, perfluorobutane sulfonic acid or perfluorooctane sulfonic acid); aliphatic $C_1$ to $C_{20}$ carboxylic acids (e.g., 2-ethyl-hexylcarboxylic acid); aliphatic perfluorocarboxylic acids (e.g., trifluoroacetic acid or perfluorooctanoic acid); aromatic sulfonic acids optionally substituted by $C_1$ to $C_{20}$ alkyl groups (e.g., benzene sulfonic acid, o-toluene sulfonic acid, p-toluene sulfonic acid or dodecylbenzene sulfonic acid); cycloalkane sulfonic acids (e.g., camphor sulfonic acid or tetrafluoroborates, hexafluorophosphates, perchlorates, hexafluoroantimonates, hexafluoroarsenates or hexachloroantimonates); and so forth. Particularly suitable counteranions are polymeric anions, such as a polymeric carboxylic or sulfonic acid (e.g., polystyrene sulfonic acid ("PSS")). The molecular weight of such polymeric anions typically ranges from about 1,000 to about 2,000,000, and in some embodiments, from about 2,000 to about 500,000.

Intrinsically conductive polymers may also be employed that have a positive charge located on the main chain that is at least partially compensated by anions covalently bound to the polymer. For example, one example of a suitable intrinsically conductive polymer may have repeating units of the following formula (III):

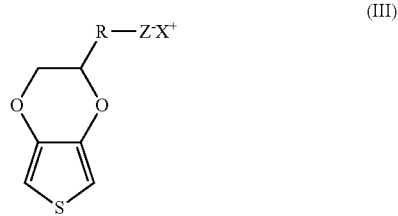

(III)

wherein,

R is $(CH_2)_a$—O—$(CH_2)_b$-L, where L is a bond or $HC([CH_2]_cH)$;

a is from 0 to 10, in some embodiments from 0 to 6, and in some embodiments, from 1 to 4 (e.g., 1);

b is from 1 to 18, in some embodiments from 1 to 10, and in some embodiments, from 2 to 6 (e.g., 2, 3, 4, or 5);

c is from 0 to 10, in some embodiments from 0 to 6, and in some embodiments, from 1 to 4 (e.g., 1);

Z is an anion, such as $SO_3^-$, $C(O)O^-$, $BF_4^-$, $CF_3SO_3^-$, $SbF_6^-$, $N(SO_2CF_3)_2^-$, $C_4H_3O_4^-$, $ClO_4^-$, etc.;

X is a cation, such as hydrogen, an alkali metal (e.g., lithium, sodium, rubidium, cesium or potassium), ammonium, etc.

In one particular embodiment, Z in formula (I) is a sulfonate ion such that the intrinsically conductive polymer contains repeating units of the following formula (IV):

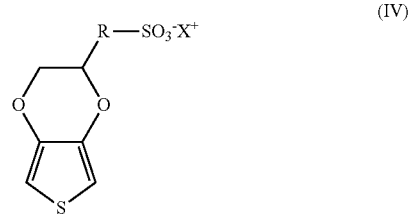

(IV)

wherein, R and X are defined above. In formula (III) or (IV), a is preferably 1 and b is preferably 3 or 4. Likewise, X is preferably sodium or potassium.

If desired, the polymer may be a copolymer that contains other types of repeating units. In such embodiments, the repeating units of formula (III) typically constitute about 50 mol. % or more, in some embodiments from about 75 mol. % to about 99 mol. %, and in some embodiments, from about 85 mol. % to about 95 mol. % of the total amount of repeating units in the copolymer. Of course, the polymer may also be a homopolymer to the extent that it contains 100 mol. % of the repeating units of formula (III). Specific examples of such homopolymers include poly(4-(2,3-dihydrothieno-[3,4-b][1,4]dioxin-2-ylmethoxy)-1-butane-sulphonic acid, salt) and poly(4-(2,3-dihydrothieno-[3,4-b][1,4]dioxin-2-ylmethoxy)-1-propanesulphonic acid, salt).

Regardless of the particular nature of the polymer, the conductive polymer particles used to form the outer layer(s) typically have an average size (e.g., diameter) of from about 1 to about 80 nanometers, in some embodiments from about 2 to about 70 nanometers, and in some embodiments, from about 3 to about 60 nanometers. The diameter of the particles may be determined using known techniques, such as by ultracentrifuge, laser diffraction, etc. The shape of the particles may likewise vary. In one particular embodiment, for instance, the particles are spherical in shape. However, it should be understood that other shapes are also contemplated by the present invention, such as plates, rods, discs, bars, tubes, irregular shapes, etc.

Although not necessarily required, the conductive polymer particles may be applied in the form of a dispersion. The concentration of the conductive polymer in the dispersion may vary depending on the desired viscosity of the dispersion and the particular manner in which the dispersion is to be applied to the capacitor element. Typically, however, the polymer constitutes from about 0.1 to about 10 wt. %, in some embodiments from about 0.4 to about 5 wt. %, and in some embodiments, from about 0.5 to about 4 wt. % of the dispersion. The dispersion may also contain one or more components to enhance the overall properties of the resulting solid electrolyte. For example, the dispersion may contain a binder to further enhance the adhesive nature of the polymeric layer and also increase the stability of the particles within the dispersion. The binder may be organic in nature, such as polyvinyl alcohols, polyvinyl pyrrolidones, polyvinyl chlorides, polyvinyl acetates, polyvinyl butyrates, polyacrylic acid esters, polyacrylic acid amides, polymethacrylic acid esters, polymethacrylic acid amides, polyacrylonitriles, styrene/acrylic acid ester, vinyl acetate/acrylic acid ester and ethylene/vinyl acetate copolymers, polybutadienes, polyisoprenes, polystyrenes, polyethers, polyesters, polycarbonates, polyurethanes, polyamides, polyimides, polysulfones, melamine formaldehyde resins, epoxide resins, silicone resins or celluloses. Crosslinking agents may also be employed to enhance the adhesion capacity of the binders. Such crosslinking agents may include, for instance, melamine compounds, masked isocyanates or crosslinkable polymers, such as polyurethanes, polyacrylates or polyolefins, and subsequent crosslinking. Dispersion agents may also be employed to facilitate the ability to apply the layer to the anode. Suitable dispersion agents include solvents, such as aliphatic alcohols (e.g., methanol, ethanol, i-propanol and butanol), aliphatic ketones (e.g., acetone and methyl ethyl ketones), aliphatic carboxylic acid esters (e.g., ethyl acetate and butyl acetate), aromatic hydrocarbons (e.g., toluene and xylene), aliphatic hydrocarbons (e.g., hexane, heptane and cyclohexane), chlorinated hydrocarbons (e.g., dichloromethane and dichloroethane), aliphatic nitriles (e.g., acetonitrile), aliphatic sulfoxides and sulfones (e.g., dimethyl sulfoxide and sulfolane), aliphatic carboxylic acid amides (e.g., methylacetamide, dimethylacetamide and dimethylformamide), aliphatic and araliphatic ethers (e.g., diethylether and anisole), water, and mixtures of any of the foregoing solvents. A particularly suitable dispersion agent is water.

In addition to those mentioned above, still other ingredients may also be used in the dispersion. For example, conventional fillers may be used that have a size of from about 10 nanometers to about 100 micrometers, in some embodiments from about 50 nanometers to about 50 micrometers, and in some embodiments, from about 100 nanometers to about 30 micrometers. Examples of such fillers include calcium carbonate, silicates, silica, calcium or barium sulfate, aluminum hydroxide, glass fibers or bulbs, wood flour, cellulose powder carbon black, electrically conductive polymers, etc. The fillers may be introduced into the dispersion in powder form, but may also be present in another form, such as fibers.

Surface-active substances may also be employed in the dispersion, such as ionic or non-ionic surfactants. Furthermore, adhesives may be employed, such as organofunctional silanes or their hydrolysates, for example 3-glycidoxypropyltrialkoxysilane, 3-aminopropyl-triethoxysilane, 3-mercaptopropyltrimethoxysilane, 3-metacryloxypropyltrimethoxysilane, vinyltrimethoxysilane or octyltriethoxysilane. The dispersion may also contain additives that increase conductivity, such as ether group-containing compounds (e.g., tetrahydrofuran), lactone group-containing compounds (e.g., γ-butyrolactone or γ-valerolactone), amide or lactam group-containing compounds (e.g., caprolactam, N-methylcaprolactam, N,N-dimethylacetamide, N-methylacetamide, N,N-dimethylformamide (DMF), N-methylformamide, N-methylformanilide, N-methylpyrrolidone (NMP), N-octylpyrrolidone, or pyrrolidone), sulfones and sulfoxides (e.g., sulfolane (tetramethylenesulfone) or dimethylsulfoxide (DMSO)), sugar or sugar derivatives (e.g., saccharose, glucose, fructose, or lactose), sugar alcohols (e.g., sorbitol or mannitol), furan derivatives (e.g., 2-furancarboxylic acid or 3-furancarboxylic acid), an alcohols (e.g., ethylene glycol, glycerol, di- or triethylene glycol).

The dispersion may be applied using a variety of known techniques, such as by spin coating, impregnation, pouring, dropwise application, injection, spraying, doctor blading, brushing, printing (e.g., ink-jet, screen, or pad printing), or dipping. The viscosity of the dispersion is typically from about 0.1 to about 100,000 mPas (measured at a shear rate of 100 s$^{-1}$), in some embodiments from about 1 to about 10,000 mPas, in some embodiments from about 10 to about 1,500 mPas, and in some embodiments, from about 100 to about 1000 mPas.

If desired, a hydroxyl-functional nonionic polymer may also be employed in the outer layer(s) of the solid electrolyte. The term "hydroxy-functional" generally means that the compound contains at least one hydroxyl functional group or is capable of possessing such a functional group in the presence of a solvent. Without intending to be limited by theory, it is believed that the use of a hydroxy-functional polymer with a certain molecular weight can minimize the likelihood of chemical decomposition at high voltages. For instance, the molecular weight of the hydroxy-functional polymer may be from about 100 to 10,000 grams per mole, in some embodiments from about 200 to 2,000, in some embodiments from about 300 to about 1,200, and in some embodiments, from about 400 to about 800.

Any of a variety of hydroxy-functional nonionic polymers may generally be employed for this purpose. In one embodiment, for example, the hydroxy-functional polymer is a polyalkylene ether. Polyalkylene ethers may include polyalkylene glycols (e.g., polyethylene glycols, polypropylene glycols polytetramethylene glycols, polyepichlorohydrins, etc.), polyoxetanes, polyphenylene ethers, polyether ketones, and so forth. Polyalkylene ethers are typically predominantly linear, nonionic polymers with terminal hydroxy groups. Particularly suitable are polyethylene glycols, polypropylene glycols and polytetramethylene glycols (polytetrahydrofurans), which are produced by polyaddition of ethylene oxide, propylene oxide or tetrahydrofuran onto water. The polyalkylene ethers may be prepared by polycondensation reactions from diols or polyols. The diol component may be selected, in particular, from saturated or unsaturated, branched or unbranched, aliphatic dihydroxy compounds containing 5 to 36 carbon atoms or aromatic dihydroxy compounds, such as, for example, pentane-1,5-diol, hexane-1,6-diol, neopentyl glycol, bis-(hydroxymethyl)-cyclohexanes, bisphenol A, dimer diols, hydrogenated dimer diols or even mixtures of the diols mentioned. In addition, polyhydric alcohols may also be used in the polymerization reaction, including for example glycerol, di- and polyglycerol, trimethylolpropane, pentaerythritol or sorbitol.

In addition to those noted above, other hydroxy-functional nonionic polymers may also be employed in the present invention. Some examples of such polymers include, for instance, ethoxylated alkylphenols; ethoxylated or propoxylated $C_6$-$C_{24}$ fatty alcohols; polyoxyethylene glycol alkyl ethers having the general formula: $CH_3$—$(CH_2)_{10\text{-}16}$—$(O$—$C_2H_4)_{1\text{-}25}$—$OH$ (e.g., octaethylene glycol monododecyl ether and pentaethylene glycol monododecyl ether); polyoxypropylene glycol alkyl ethers having the general formula: $CH_3$—$(CH_2)_{10\text{-}16}$—$(O$—$C_3H_6)_{1\text{-}25}$—$OH$; polyoxyethylene glycol octylphenol ethers having the following general formula: $C_8H_{17}$—$(C_6H_4)$—$(O$—$C_2H_4)_{1\text{-}25}$—$OH$ (e.g., Triton™ X-100); polyoxyethylene glycol alkylphenol ethers having the following general formula: $C_9H_{19}$—$(C_6H_4)$—$(O$—$C_2H_4)_{1\text{-}25}$—$OH$ (e.g., nonoxynol-9); polyoxyethylene glycol esters of $C_8$-$C_{24}$ fatty acids, such as polyoxyethylene glycol sorbitan alkyl esters (e.g., polyoxyethylene (20) sorbitan monolaurate, polyoxyethylene (20) sorbitan monopalmitate, polyoxyethylene (20) sorbitan monostearate, polyoxyethylene (20) sorbitan monooleate, PEG-20 methyl glucose distearate, PEG-20 methyl glucose sesquistearate, PEG-80 castor oil, and PEG-20 castor oil, PEG-3 castor oil, PEG 600 dioleate, and PEG 400 dioleate) and polyoxyethylene glycerol alkyl esters (e.g., polyoxyethylene-23 glycerol laurate and polyoxyethylene-20 glycerol stearate); polyoxyethylene glycol ethers of $C_8$-$C_{24}$ fatty acids (e.g., polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, polyoxyethylene-20 isohexadecyl ether, polyoxyethylene-15 tridecyl ether, and polyoxyethylene-6 tridecyl ether); block copolymers of polyethylene glycol and polypropylene glycol (e.g., Poloxamers); and so forth, as well as mixtures thereof.

The hydroxy-functional nonionic polymer may be incorporated into the outer layers in a variety of different ways. In certain embodiments, for instance, the nonionic polymer may simply be incorporated into a dispersion of conductive polymers. In such embodiments, the concentration of the nonionic polymer in the layer may be from about 1 wt. % to about 50 wt. %, in some embodiments from about 5 wt. % to about 40 wt. %, and in some embodiments, from about 10 wt. % to about 30 wt. %. In other embodiments, however, the nonionic polymer may be applied after the initial outer layer(s) are formed. In such embodiments, the technique used to apply the nonionic polymer may vary. For example, the nonionic polymer may be applied in the form of a liquid solution using various methods, such as immersion, dipping, pouring, dripping, injection, spraying, spreading, painting or printing, for example, inkjet, or screen printing. Solvents known to the person skilled in the art can be employed in the solution, such as water, alcohols, or a mixture thereof. The concentration of the nonionic polymer in such a solution typically ranges from about 5 wt. % to about 95 wt. %, in some embodiments from about 10 wt. % to about 70 wt. %, and in some embodiments, from about 15 wt. % to about 50 wt. % of the solution. If desired, such solutions may be generally free of conductive polymers. For example, conductive polymers may constitute about 2 wt. % or less, in some embodiments about 1 wt. % or less, and in some embodiments, about 0.5 wt. % or less of the solution.

D. Pre-Coat Layer

If desired, an optional pre-coat layer may be employed that overlies the dielectric that is optionally positioned between the dielectric and the solid electrolyte. The pre-coat layer may contain any of a variety of different materials. In one embodiment, for example, the pre-coat layer includes an organometallic compound having the following general formula:

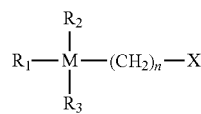

wherein,

M is an organometallic atom, such as silicon, titanium, and so forth;

$R_1$, $R_2$, and $R_3$ are independently an alkyl (e.g., methyl, ethyl, propyl, etc.) or a hydroxyalkyl (e.g., hydroxymethyl, hydroxyethyl, hydroxypropyl, etc.), wherein at least one of $R_1$, $R_2$, and $R_3$ is a hydroxyalkyl;

n is an integer from 0 to 8, in some embodiments from 1 to 6, and in some embodiments, from 2 to 4 (e.g., 3); and X is an organic or inorganic functional group, such as glycidyl, glycidyloxy, mercapto, amino, vinyl, etc.

In certain embodiments, $R_1$, $R_2$, and $R_3$ may a hydroxyalkyl (e.g., $OCH_3$). In other embodiments, however, $R_1$ may be an alkyl (e.g., $CH_3$) and $R_2$ and $R_3$ may a hydroxyalkyl (e.g., $OCH_3$).

Further, in certain embodiments, M may be silicon so that the organometallic compound is an organosilane compound, such as an alkoxysilane. Suitable alkoxysilanes may include, for instance, 3-aminopropyltrimethoxysilane, 3-aminopropyltriethoxysilane, 3-aminopropylmethyldimethoxysilane, 3-aminopropylmethyldiethoxysilane, 3-(2-aminoethyl)aminopropyltrimethoxysilane, 3-mercaptopropyltrimethoxysilane, 3-mercaptopropyltriethoxysilane, 3-mercaptopropylmethyldimethoxysilane, 3-mercaptopropylmethyldiethoxysilane, glycidoxymethyltrimethoxysilane, glycidoxymethyltriethoxysilane, glycidoxymethyltripropoxysilane, glycidoxymethyltributoxysilane, β-glycidoxyethyltrimethoxysilane, β-glycidoxyethyltriethoxysilane, β-glycidoxyethyltripropoxysilane, β-glycidoxyethyltributoxysilane, β-glycidoxyethyltrimethoxysilane, α-glycidoxyethyltriethoxysilane, α-glycidoxyethyltripropoxysilane, α-glycidoxyethyltributoxysilane, γ-glycidoxypropyltrimethoxysilane, γ-glycidoxypropyltriethoxysilane, γ-glycidoxypropyl-tripropoxysilane, γ-glycidoxypropyltributoxysilane, β-glycidoxypropyltrimethoxysilane, β-glycidoxypropyl-triethoxysilane, β-glycidoxypropyl-tripropoxysilane, α-glycidoxypropyltributoxysilane, α-glycidoxypropyltrimethoxysilane, α-glycidoxypropyltriethoxysilane, α-glycidoxypropyl-tripropoxysilane, α-glycidoxypropyltributoxysilane, γ-glycidoxybutyltrimethoxysilane, δ-glycidoxybutyltriethoxysilane, δ-glycidoxybutyltripropoxysilane, δ-glycidoxybutyl-tributoxysilane, δ-glycidoxybutyltrimethoxysilane, γ-glycidoxybutyltriethoxysilane, γ-glycidoxybutyltripropoxysilane, γ-propoxybutyltributoxysilane, δ-glycidoxybutyltrimethoxysilane, δ-glycidoxybutyltriethoxysilane, δ-glycidoxybutyltripropoxysilane, α-glycidoxybutyltrimethoxysilane, α-glycidoxybutyltriethoxysilane, α-glycidoxybutyl-tripropoxysilane, α-glycidoxybutyltributoxysilane, (3,4-epoxycyclohexyl)-methyl-trimethoxysilane, (3,4-epoxycyclohexyl)methyl-triethoxysilane, (3,4-epoxycyclohexyl)methyltripropoxysilane, (3,4-epoxycyclohexyl)-methyl-tributoxysilane, (3,4-epoxycyclohexyl)ethyl-trimethoxysilane, (3,4-epoxycyclohexyl)ethyl-triethoxysilane, (3,4-epoxycyclohexyl)ethyltripropoxysilane, (3,4-epoxycyclohexyl)ethyltributoxysilane, (3,4-epoxycyclohexyl)propyltrimethoxysilane, (3,4-epoxycyclohexyl)propyltriethoxysilane, (3,4-epoxycyclohexyl)propyl-tripropoxysilane, (3,4-epoxycyclohexyl)propyltributoxysilane, (3,4-epoxycyclohexyl)butyltrimethoxysilane, (3,4-epoxycyclohexyl)butyltriethoxysilane, (3,4-epoxycyclohexyl)butyltripropoxysilane, (3,4-epoxycyclohexyl)butyltributoxysilane, and so forth.

The particular manner in which the pre-coat layer is applied to the capacitor body may vary as desired. In one particular embodiment, the compound is dissolved in an organic solvent and applied to the part as a solution, such as by screen-printing, dipping, electrophoretic coating, spraying, etc. The organic solvent may vary, but is typically an alcohol, such as methanol, ethanol, etc. Organometallic compounds may constitute from about 0.1 wt. % to about 10 wt. %, in some embodiments from about 0.2 wt. % to about 8 wt. %, and in some embodiments, from about 0.5 wt. % to about 5 wt. % of the solution. Solvents may likewise constitute from about 90 wt. % to about 99.9 wt. %, in some embodiments from about 92 wt. % to about 99.8 wt. %, and in some embodiments, from about 95 wt. % to about 99.5 wt. % of the solution. Once applied, the part may then be dried to remove the solvent therefrom and form a pre-coat layer containing the organometallic compound.

E. External Polymer Coating

An external polymer coating may also be optionally employed that overlies the solid electrolyte. When employed, the external polymer coating typically contains one or more layers formed from pre-polymerized conductive polymer particles such as described above (e.g., dispersion of extrinsically conductive polymer particles). The external coating may be able to further penetrate into the edge region of the capacitor body to increase the adhesion to the dielectric and result in a more mechanically robust part, which may reduce equivalent series resistance and leakage current. Because it is generally intended to improve the degree of edge coverage rather to impregnate the interior of the anode body, the particles used in the external coating may have a larger size than those employed in the outer layers of the solid electrolyte. For example, the ratio of the average size of the particles employed in the external polymer coating to the average size of the particles employed in any dispersion of the solid electrolyte is typically from about 1.5 to about 30, in some embodiments from about 2 to about 20, and in some embodiments, from about 5 to about 15. For example, the particles employed in the dispersion of the external coating may have an average size of from about 80 to about 500 nanometers, in some embodiments from about 90 to about 250 nanometers, and in some embodiments, from about 100 to about 200 nanometers.

If desired, a crosslinking agent may also be employed in the external polymer coating to enhance the degree of adhesion to the solid electrolyte. Typically, the crosslinking agent is applied prior to application of the dispersion used in the external coating. Suitable crosslinking agents are described, for instance, in U.S. Patent Publication No. 2007/0064376 to Merker, et al. and include, for instance, amines (e.g., diamines, triamines, oligomer amines, polyamines, etc.); polyvalent metal cations, such as salts or compounds of Mg, Al, Ca, Fe, Cr, Mn, Ba, Ti, Co, Ni, Cu, Ru, Ce or Zn, phosphonium compounds, sulfonium compounds, etc. Particularly suitable examples include, for instance, 1,4-diaminocyclohexane, 1,4-bis(amino-methyl)cyclohexane, ethylenediamine, 1,6-hexanediamine, 1,7-heptanediamine, 1,8-octanediamine, 1,9-nonanediamine, 1,10-decanediamine, 1,12-dodecanediamine, N,N-dimethylethylenediamine, N,N,N',N'-tetramethylethylenediamine, N,N,N',N'-tetramethyl-1,4-butanediamine, etc., as well as mixtures thereof.

The crosslinking agent is typically applied from a solution or dispersion whose pH is from 1 to 10, in some embodiments from 2 to 7, in some embodiments, from 3 to 6, as determined at 25° C. Acidic compounds may be employed to help achieve the desired pH level. Examples of solvents or dispersants for the crosslinking agent include water or organic solvents, such as alcohols, ketones, carboxylic esters, etc. The crosslinking agent may be applied to the capacitor body by any known process, such as spin-coating, impregnation, casting, dropwise application, spray application, vapor deposition, sputtering, sublimation, knife-coating, painting or printing, for example inkjet, screen or pad printing. Once applied, the crosslinking agent may be dried prior to application of the polymer dispersion. This process may then be repeated until the desired thickness is achieved. For example, the total thickness of the entire external polymer coating, including the crosslinking agent and dispersion layers, may range from about 1 to about 50 µm, in some embodiments from about 2 to about 40 µm, and in some embodiments, from about 5 to about 20 µm.

F. Other Optional Components

If desired, the capacitor element may also contain other layers as is known in the art. For example, an adhesive layer may optionally be formed between the dielectric and solid electrolyte. The adhesive layer may, for instance, be present between the dielectric and pre-coat layer and/or between the pre-coat layer and the solid electrolyte. Regardless, the adhesive layer is typically formed from a relatively insulative resinous material (natural or synthetic). Such materials may have a specific resistivity of greater than about 10 Ω·cm, in some embodiments greater than about 100, in some embodiments greater than about 1,000 Ω·cm, in some embodiments greater than about $1 \times 10^5$ Ω·cm, and in some embodiments, greater than about $1 \times 10^{10}$ Ω·cm. Some resinous materials that may be utilized in the present invention include, but are not limited to, polyurethane, polystyrene, esters of unsaturated or saturated fatty acids (e.g., glycerides), and so forth. For instance, suitable esters of fatty acids include, but are not limited to, esters of lauric acid, myristic acid, palmitic acid, stearic acid, eleostearic acid, oleic acid, linoleic acid, inolenic acid, aleuritic acid, shellolic acid, and so forth. These esters of fatty acids have been found particularly useful when used in relatively complex combinations to form a "drying oil", which allows the resulting film to rapidly polymerize into a stable layer. Such drying oils may include mono-, di-, and/or tri-glycerides, which have a glycerol backbone with one, two, and three, respectively, fatty acyl residues that are esterified. For instance, some suitable drying oils that may be used include, but are not limited to, olive oil, linseed oil, castor oil, tung oil, soybean oil, and shellac. These and other adhesive layer materials are described in more detail U.S. Pat. No. 6,674,635 to Fife, et al.

If desired, the part may also be applied with a carbon layer (e.g., graphite) and silver layer, respectively. The silver coating may, for instance, act as a solderable conductor, contact layer, and/or charge collector for the capacitor and the carbon coating may limit contact of the silver coating with the solid electrolyte. Such coatings may cover some or all of the solid electrolyte.

II. Terminations

Once formed, the capacitor element may be provided with terminations, particularly when employed in surface mounting applications. For example, the capacitor may contain an anode termination to which an anode lead of the capacitor element is electrically connected and a cathode termination to which the cathode of the capacitor element is electrically connected. Any conductive material may be employed to form the terminations, such as a conductive metal (e.g., copper, nickel, silver, nickel, zinc, tin, palladium, lead, copper, aluminum, molybdenum, titanium, iron, zirconium, magnesium, and alloys thereof). Particularly suitable conductive metals include, for instance, copper, copper alloys (e.g., copper-zirconium, copper-magnesium, copper-zinc, or copper-iron), nickel, and nickel alloys (e.g., nickel-iron). The thickness of the terminations is generally selected to minimize the thickness of the capacitor. For instance, the thickness of the terminations may range from about 0.05 to about 1 millimeter, in some embodiments from about 0.05 to about 0.5 millimeters, and from about 0.07 to about 0.2 millimeters. One exemplary conductive material is a copper-iron alloy metal plate available from Wieland (Germany). If desired, the surface of the terminations may be electroplated with nickel, silver, gold, tin, etc. as is known in the art to ensure that the final part is mountable to the circuit board. In one particular embodiment, both surfaces of the terminations are plated with nickel and silver flashes, respectively, while the mounting surface is also plated with a tin solder layer.

The terminations may be connected to the capacitor element using any technique known in the art. In one embodiment, for example, a lead frame may be provided that defines the cathode termination and anode termination. To attach the electrolytic capacitor element to the lead frame, a conductive adhesive may initially be applied to a surface of the cathode termination. The conductive adhesive may include, for instance, conductive metal particles contained with a resin composition. The metal particles may be silver, copper, gold, platinum, nickel, zinc, bismuth, etc. The resin composition may include a thermoset resin (e.g., epoxy resin), curing agent (e.g., acid anhydride), and compound (e.g., silane compounds). Suitable conductive adhesives may be described in U.S. Patent Application Publication No. 2006/0038304 to Osako, et al. Any of a variety of techniques may be used to apply the conductive adhesive to the cathode termination. Printing techniques, for instance, may be employed due to their practical and cost-saving benefits. The anode lead may also be electrically connected to the anode termination using any technique known in the art, such as mechanical welding, laser welding, conductive adhesives, etc. Upon electrically connecting the anode lead to the anode termination, the conductive adhesive may then be cured to ensure that the electrolytic capacitor element is adequately adhered to the cathode termination.

III. Housing

Due to the ability of the capacitor to exhibit good electrical performance in various environments, it is not necessary for the capacitor element to be hermetically sealed within a housing. Nevertheless, in certain embodiments, it may be desired to hermetically seal the capacitor element within a housing. In one embodiment, for example, the capacitor element may be hermetically sealed within a housing in the presence of a gaseous atmosphere that contains an inert gas, thereby further limiting the amount of moisture supplied to the solid electrolyte of the capacitor element.

The capacitor element may be sealed within a housing in various ways. In certain embodiments, for instance, the capacitor element may be enclosed within a case, which may then be filled with a resinous material, such as a thermoset resin (e.g., epoxy resin) that can be cured to form a hardened housing. Examples of such resins include, for instance, epoxy resins, polyimide resins, melamine resins, urea-formaldehyde resins, polyurethane resins, phenolic resins, polyester resins, etc. Epoxy resins are also particularly suitable. Still other additives may also be employed, such as photoinitiators, viscosity modifiers, suspension aiding agents, pigments, stress reducing agents, non-conductive fillers, stabilizers, etc. For example, the non-conductive fillers may include inorganic oxide particles, such as silica, alumina, zirconia, magnesium oxide, iron oxide, copper oxide, zeolites, silicates, clays (e.g., smectite clay), etc., as well as composites (e.g., alumina-coated silica particles) and mixtures thereof. Regardless, the resinous material may surround and encapsulate the capacitor element so that at least a portion of the anode and cathode terminations are exposed for mounting onto a circuit board. When encapsulated in this manner, the capacitor element and resinous material form an integral capacitor.

Of course, in alternative embodiments, it may be desirable to enclose the capacitor element within a housing that remains separate and distinct. In this manner, the atmosphere of the housing may be gaseous and contain at least one inert gas, such as nitrogen, helium, argon, xenon, neon, krypton, radon, and so forth, as well as mixtures thereof. Typically, inert gases constitute the majority of the atmosphere within the housing, such as from about 50 wt. % to 100 wt. %, in some embodiments from about 75 wt. % to 100 wt. %, and in some embodiments, from about 90 wt. % to about 99 wt. % of the atmosphere. If desired, a relatively small amount of non-inert gases may also be employed, such as carbon dioxide, oxygen, water vapor, etc. In such cases, however, the non-inert gases typically constitute 15 wt. % or less, in some embodiments 10 wt. % or less, in some embodiments about 5 wt. % or less, in some embodiments about 1 wt. % or less, and in some embodiments, from about 0.01 wt. % to about 1 wt. % of the atmosphere within the housing.

Any of a variety of different materials may be used to form the housing, such as metals, plastics, ceramics, and so forth. In one embodiment, for example, the housing includes one or more layers of a metal, such as tantalum, niobium, aluminum, nickel, hafnium, titanium, copper, silver, steel (e.g., stainless), alloys thereof (e.g., electrically conductive oxides), composites thereof (e.g., metal coated with electrically conductive oxide), and so forth. In another embodiment, the housing may include one or more layers of a ceramic material, such as aluminum nitride, aluminum oxide, silicon oxide, magnesium oxide, calcium oxide, glass, etc., as well as combinations thereof.

The housing may have any desired shape, such as cylindrical, D-shaped, rectangular, triangular, prismatic, etc. Referring to FIG. 1, for example, one embodiment of a capacitor 100 is shown that contains a housing 122 and a capacitor element 120. In this particular embodiment, the housing 122 is generally rectangular. Typically, the housing and the capacitor element have the same or similar shape so that the capacitor element can be readily accommodated within the interior cavity. In the illustrated embodiment, for example, both the capacitor element 120 and the housing 122 have a generally rectangular shape.

If desired, the capacitor of the present invention may exhibit a relatively high volumetric efficiency. To facilitate such high efficiency, the capacitor element typically occupies a substantial portion of the volume of an interior cavity of the housing. For example, the capacitor element may occupy about 30 vol. % or more, in some embodiments about 50 vol. % or more, in some embodiments about 60 vol. % or more, in some embodiments about 70 vol. % or more, in some embodiments from about 80 vol. % to about 98 vol. %, and in some embodiments, from about 85 vol. % to 97 vol. % of the interior cavity of the housing. To this end, the difference between the dimensions of the capacitor element and those of the interior cavity defined by the housing are typically relatively small.

Referring to FIG. 1, for example, the capacitor element 120 may have a length (excluding the length of the anode lead 6) that is relatively similar to the length of an interior cavity 126 defined by the housing 122. For example, the ratio of the length of the anode to the length of the interior cavity ranges from about 0.40 to 1.00, in some embodiments from about 0.50 to about 0.99, in some embodiments from about 0.60 to about 0.99, and in some embodiments, from about 0.70 to about 0.98. The capacitor element 120 may have a length of from about 5 to about 10 millimeters, and the interior cavity 126 may have a length of from about 6 to about 15 millimeters. Similarly, the ratio of the height of the capacitor element 120 (in the −z direction) to the height of the interior cavity 126 may range from about 0.40 to 1.00, in some embodiments from about 0.50 to about 0.99, in some embodiments from about 0.60 to about 0.99, and in some embodiments, from about 0.70 to about 0.98. The ratio of the width of the capacitor element 120 (in the −x direction) to the width of the interior cavity 126 may also range from about 0.50 to 1.00, in some embodiments from about 0.60 to about 0.99, in some embodiments from about 0.70 to about 0.99, in some embodiments from about 0.80 to about 0.98, and in some embodiments, from about 0.85 to about 0.95. For example, the width of the capacitor element 120 may be from about 2 to about 7 millimeters and the width of the interior cavity 126 may be from about 3 to about 10 millimeters, and the height of the capacitor element 120 may be from about 0.5 to about 2 millimeters and the width of the interior cavity 126 may be from about 0.7 to about 6 millimeters.

Although by no means required, the capacitor element may be attached to the housing in such a manner that an anode termination and cathode termination are formed external to the housing for subsequent integration into a circuit. The particular configuration of the terminations may depend on the intended application. In one embodiment, for example, the capacitor may be formed so that it is surface mountable, and yet still mechanically robust. For example, the anode lead may be electrically connected to external, surface mountable anode and cathode terminations (e.g., pads, sheets, plates, frames, etc.). Such terminations may extend through the housing to connect with the capacitor. The thickness or height of the terminations is generally selected to minimize the thickness of the capacitor. For instance, the thickness of the terminations may range from about 0.05 to about 1 millimeter, in some embodiments from about 0.05 to about 0.5 millimeters, and from about 0.1 to about 0.2 millimeters. If desired, the surface of the terminations may be electroplated with nickel, silver, gold, tin, etc. as is known in the art to ensure that the final part is mountable to the circuit board. In one particular embodiment, the termination(s) are deposited with nickel and silver flashes, respectively, and the mounting surface is also plated with a tin solder layer. In another embodiment, the termination(s) are deposited with thin outer metal layers (e.g., gold) onto a base metal layer (e.g., copper alloy) to further increase conductivity.

In certain embodiments, connective members may be employed within the interior cavity of the housing to facilitate connection to the terminations in a mechanically stable manner. For example, referring again to FIG. 1, the capacitor 100 may include a connection member 162 that is formed from a first portion 167 and a second portion 165. The connection member 162 may be formed from conductive materials similar to the external terminations. The first portion 167 and second portion 165 may be integral or separate pieces that are connected together, either directly or via an additional conductive element (e.g., metal). In the illustrated embodiment, the second portion 165 is provided in a plane that is generally parallel to a lateral direction in which the lead 6 extends (e.g., -y direction). The first portion 167 is "upstanding" in the sense that it is provided in a plane that is generally perpendicular the lateral direction in which the lead 6 extends. In this manner, the first portion 167 can limit movement of the lead 6 in the horizontal direction to enhance surface contact and mechanical stability during use. If desired, an insulative material 7 (e.g., Teflon™ washer) may be employed around the lead 6.

The first portion 167 may possess a mounting region (not shown) that is connected to the anode lead 6. The region may have a "U-shape" for further enhancing surface contact and mechanical stability of the lead 6. Connection of the region to the lead 6 may be accomplished using any of a variety of known techniques, such as welding, laser welding, conductive adhesives, etc. In one particular embodiment, for example, the region is laser welded to the anode lead 6. Regardless of the technique chosen, however, the first portion 167 can hold the anode lead 6 in substantial horizontal alignment to further enhance the dimensional stability of the capacitor 100.

Referring again to FIG. 1, one embodiment of the present invention is shown in which the connective member 162 and capacitor element 120 are connected to the housing 122 through anode and cathode terminations 127 and 129, respectively. More specifically, the housing 122 of this embodiment includes an outer wall 123 and two opposing sidewalls 124 between which a cavity 126 is formed that includes the capacitor element 120. The outer wall 123 and sidewalls 124 may be formed from one or more layers of a metal, plastic, or ceramic material such as described above. In this particular embodiment, the anode termination 127 contains a first region 127a that is positioned within the housing 122 and electrically connected to the connection member 162 and a second region 127b that is positioned external to the housing 122 and provides a mounting surface 201. Likewise, the cathode termination 129 contains a first region 129a that is positioned within the housing 122 and electrically connected to the solid electrolyte of the capacitor element 120 and a second region 129b that is positioned external to the housing 122 and provides a mounting surface 203. It should be understood that the entire portion of such regions need not be positioned within or external to the housing.

In the illustrated embodiment, a conductive trace 127c extends in the outer wall 123 of the housing to connect the first region 127a and second region 127b. Similarly, a conductive trace 129c extends in the outer wall 123 of the housing to connect the first region 127a and second region 127b. The conductive traces and/or regions of the terminations may be separate or integral. In addition to extending through the outer wall of the housing, the traces may also be positioned at other locations, such as external to the outer wall. Of course, the present invention is by no means limited to the use of conductive traces for forming the desired terminations.

Regardless of the particular configuration employed, connection of the terminations 127 and 129 to the capacitor element 120 may be made using any known technique, such as welding, laser welding, conductive adhesives, etc. In one particular embodiment, for example, a conductive adhesive 131 is used to connect the second portion 165 of the connection member 162 to the anode termination 127. Likewise, a conductive adhesive 133 is used to connect the cathode of the capacitor element 120 to the cathode termination 129.

Optionally, a polymeric restraint may also be disposed in contact with one or more surfaces of the capacitor element, such as the rear surface, front surface, upper surface, lower surface, side surface(s), or any combination thereof. The polymeric restraint can reduce the likelihood of delamination by the capacitor element from the housing. In this regard, the polymeric restraint may possesses a certain degree of strength that allows it to retain the capacitor element in a relatively fixed positioned even when it is subjected to vibrational forces, yet is not so strong that it cracks. For example, the restraint may possess a tensile strength of from about 1 to about 150 Megapascals ("MPa"), in some embodiments from about 2 to about 100 MPa, in some embodiments from about 10 to about 80 MPa, and in some embodiments, from about 20 to about 70 MPa, measured at a temperature of about 25° C. It is normally desired that the restraint is not electrically conductive. Referring again to FIG. 1, for instance, one embodiment is shown in which a single polymeric restraint 197 is disposed in contact with an upper surface 181 and rear surface 177 of the capacitor element 120. While a single restraint is shown in FIG. 1, it should be understood that separate restraints may be employed to accomplish the same function. In fact, more generally, any number of polymeric restraints may be employed to contact any desired surface of the capacitor element. When multiple restraints are employed, they may be in contact with each other or remain physically separated. For example, in one embodiment, a second polymeric restraint (not shown) may be employed that contacts the upper surface 181 and front surface 179 of the capacitor element 120. The first polymeric restraint 197 and the second polymeric restraint (not shown) may or may not be in contact with each other. In yet another embodiment, a polymeric restraint may also contact a lower surface 183 and/or side surface(s) of the capacitor element 120, either in conjunction with or in lieu of other surfaces.

Regardless of how it is applied, it is typically desired that the polymeric restraint is also in contact with at least one surface of the housing to help further mechanically stabilize the capacitor element against possible delamination. For example, the restraint may be in contact with an interior surface of one or more sidewall(s), outer wall, lid, etc. In FIG. 1, for example, the polymeric restraint 197 is in contact with an interior surface 107 of sidewall 124 and an interior surface 109 of outer wall 123. While in contact with the housing, it is nevertheless desired that at least a portion of the cavity defined by the housing remains unoccupied to allow for the inert gas to flow through the cavity and limit contact of the solid electrolyte with oxygen. For example, at least about 5% of the cavity volume typically remains unoccupied by the capacitor element and polymer restraint, and in some embodiments, from about 10% to about 50% of the cavity volume.

Once connected in the desired manner, the resulting package is hermetically sealed as described above. Referring again to FIG. 1, for instance, the housing 122 may also include a lid 125 that is placed on an upper surface of side walls 124 after the capacitor element 120 and the polymer restraint 197 are positioned within the housing 122. The lid 125 may be formed from a ceramic, metal (e.g., iron, copper, nickel, cobalt, etc., as well as alloys thereof), plastic, and so forth. If desired, a sealing member 187 may be disposed between the lid 125 and the side walls 124 to help provide a good seal. In one embodiment, for example, the sealing member may include a glass-to-metal seal, Kovar® ring (Goodfellow Camridge, Ltd.), etc. The height of the side walls 124 is generally such that the lid 125 does not contact any surface of the capacitor element 120 so that it is not contaminated. The polymeric restraint 197 may or may not contact the lid 125. When placed in the desired position, the lid 125 is hermetically sealed to the sidewalls 124 using known techniques, such as welding (e.g., resistance welding, laser welding, etc.), soldering, etc. Hermetic sealing generally occurs in the presence of inert gases as described above so that the resulting assembly is substantially free of reactive gases, such as oxygen or water vapor.

Figure 2:
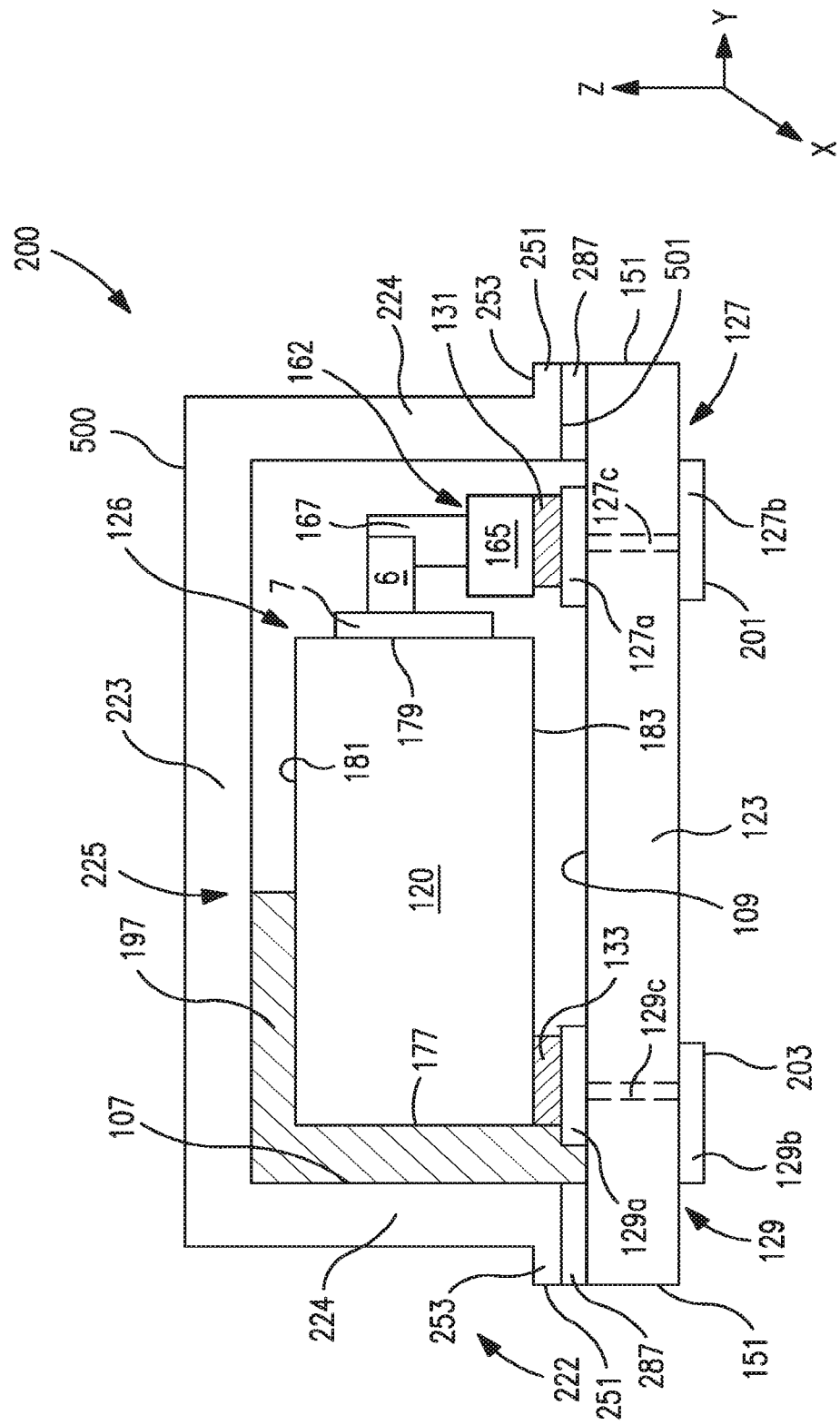
FIG. 2 is a cross-sectional view of another embodiment of a capacitor of the assembly of the present invention.

It should be understood that the embodiments described are only exemplary, and that various other configurations may be employed in the present invention for hermetically sealing a capacitor element within a housing. Referring to FIG. 2, for instance, another embodiment of a capacitor 200 is shown that employs a housing 222 that includes an outer wall 123 and a lid 225 between which a cavity 126 is formed that includes the capacitor element 120 and polymeric restraint 197. The lid 225 includes an outer wall 223 that is integral with at least one sidewall 224. In the illustrated embodiment, for example, two opposing sidewalls 224 are shown in cross-section. The outer walls 223 and 123 both extend in a lateral direction (−y direction) and are generally parallel with each other and to the lateral direction of the anode lead 6. The sidewall 224 extends from the outer wall 223 in a longitudinal direction that is generally perpendicular to the outer wall 123. A distal end 500 of the lid 225 is defined by the outer wall 223 and a proximal end 501 is defined by a lip 253 of the sidewall 224.

The lip 253 extends from the sidewall 224 in the lateral direction, which may be generally parallel to the lateral direction of the outer wall 123. The angle between the sidewall 224 and the lip 253 may vary, but is typically from about 60° to about 120°, in some embodiments from about 70° to about 110°, and in some embodiments, from about 80° to about 100° (e.g., about 90°). The lip 253 also defines a peripheral edge 251, which may be generally perpendicular to the lateral direction in which the lip 253 and outer wall 123 extend. The peripheral edge 251 is located beyond the outer periphery of the sidewall 224 and may be generally coplanar with an edge 151 of the outer wall 123. The lip 253 may be sealed to the outer wall 123 using any known technique, such as welding (e.g., resistance or laser), soldering, glue, etc. For example, in the illustrated embodiment, a sealing member 287 is employed (e.g., glass-to-metal seal, Kovar® ring, etc.) between the components to facilitate their attachment. Regardless, the use of a lip described above can enable a more stable connection between the components and improve the seal and mechanical stability of the capacitor.

Figure 3:
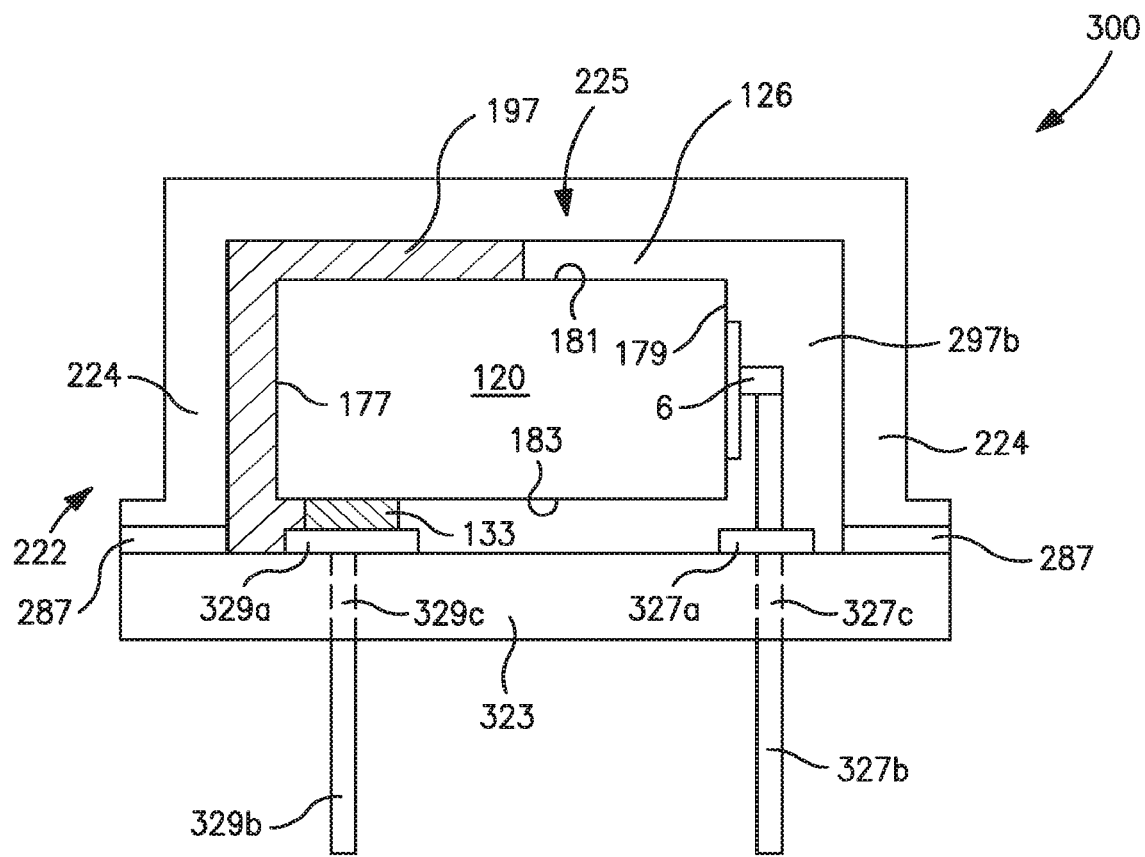
FIG. 3 is a cross-sectional view of yet another embodiment of a capacitor of the assembly of the present invention.

Still other possible housing configurations may be employed in the present invention. For example, FIG. 3 shows a capacitor 300 having a housing configuration similar to that of FIG. 2, except that terminal pins 327b and 329b are employed as the external terminations for the anode and cathode, respectively. More particularly, the terminal pin 327a extends through a trace 327c formed in the outer wall 323 and is connected to the anode lead 6 using known techniques (e.g., welding). An additional section 327a may be employed to secure the pin 327b. Likewise, the terminal pin 329b extends through a trace 329c formed in the outer wall 323 and is connected to the cathode via a conductive adhesive 133 as described above.

Figure 4:
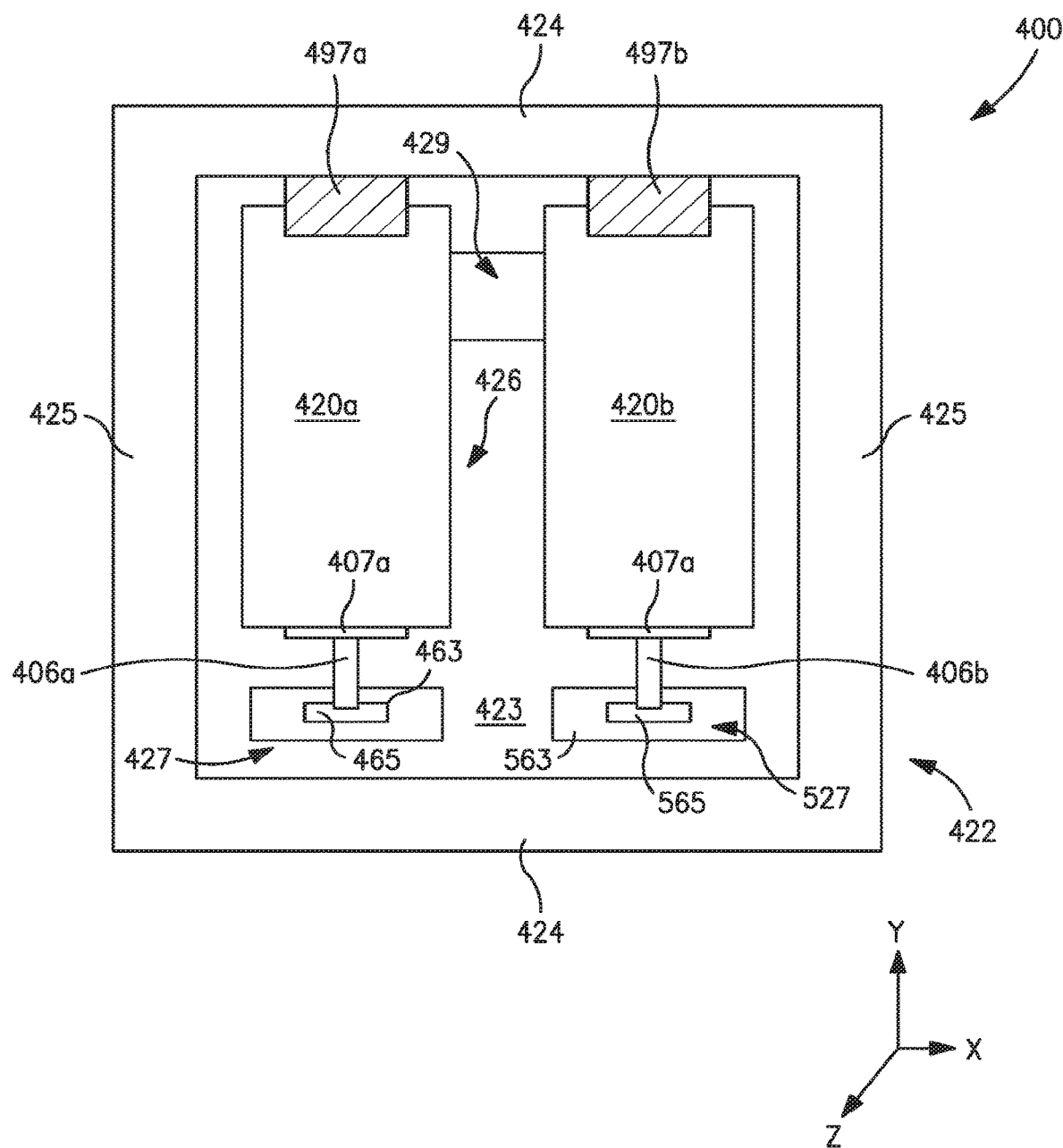
FIG. 4 is a top view of still another embodiment of a capacitor of the assembly of the present invention.

The embodiments shown in FIGS. 1-3 are discussed herein in terms of only a single capacitor element. It should also be understood, however, that multiple capacitor elements may also be hermetically sealed within a housing. The multiple capacitor elements may be attached to the housing using any of a variety of different techniques. Referring to FIG. 4, for example one particular embodiment of a capacitor 400 that contains two capacitor elements is shown and will now be described in more detail. More particularly, the capacitor 400 includes a first capacitor element 420a in electrical communication with a second capacitor element 420b. In this embodiment, the capacitor elements are aligned so that their major surfaces are in a horizontal configuration. That is, a major surface of the capacitor element 420a defined by its width (−x direction) and length (−y direction) is positioned adjacent to a corresponding major surface of the capacitor element 420b. Thus, the major surfaces are generally coplanar. Alternatively, the capacitor elements may be arranged so that their major surfaces are not coplanar, but perpendicular to each other in a certain direction, such as the −z direction or the −x direction. Of course, the capacitor elements need not extend in the same direction.

The capacitor elements 420a and 420b are positioned within a housing 422 that contains an outer wall 423 and sidewalls 424 and 425 that together define a cavity 426. Although not shown, a lid may be employed that covers the upper surfaces of the sidewalls 424 and 425 and seals the assembly 400 as described above. Optionally, a polymeric restraint may also be employed to help limit the vibration of the capacitor elements. In FIG. 4, for example, separate polymer restraints 497a and 497b are positioned adjacent to and in contact with the capacitor elements 420a and 420b, respectively. The polymer restraints 497a and 497b may be positioned in a variety of different locations. Further, one of the restraints may be eliminated, or additional restraints may be employed. In certain embodiments, for example, it may be desired to employ a polymeric restraint between the capacitor elements to further improve mechanical stability.

In addition to the capacitor elements, the capacitor also contains an anode termination to which anode leads of respective capacitor elements are electrically connected and a cathode termination to which the cathodes of respective capacitor elements are electrically connected. Referring again to FIG. 4, for example, the capacitor elements are shown connected in parallel to a common cathode termination 429. In this particular embodiment, the cathode termination 429 is initially provided in a plane that is generally parallel to the bottom surface of the capacitor elements and may be in electrical contact with conductive traces (not shown). The capacitor 400 also includes connective members 427 and 527 that are connected to anode leads 407a and 407b, respectively, of the capacitor elements 420a and 420b. More particularly, the connective member 427 contains an upstanding portion 465 and a planar portion 463 that is in connection with an anode termination (not shown). Likewise, the connective 527 contains an upstanding portion 565 and a planar portion 563 that is in connection with an anode termination (not shown).

The present invention may be better understood by reference to the following examples.

Test Procedures

Breakdown Voltage

The breakdown voltage may be measured using Keithley 2400 SourceMeter at the temperature 23° C.±2° C. An individual capacitor may be charged with constant current determined by the equation:

Current $(A)$=Nominal Capacitance $(F)\times dU/dt$, where dU/dt represents the voltage slope and is typically set to 10 V/s. Voltage is measured during charging. When the applied voltage decreases more than 10%, the maximum achieved voltage value is recorded as the "breakdown voltage." When measuring multiple samples, a minimum, maximum, and average breakdown voltage may be recorded.

Dielectric Thickness

The dielectric thickness may be measured using a Zeiss Sigma FESEM at 20,000× to 50,000× magnification. Samples may be prepared by cutting a finished part in a plane perpendicular to the longest dimension of the finished part. Thickness measurement may be done at sites where the cut was in a perpendicular direction through the dielectric layer. When measuring multiple samples, an average dielectric thickness may be recorded.

Dielectric Strength

The dielectric strength may be calculated by dividing the breakdown voltage (V) for a sample by the average dielectric thickness (nm). When multiple samples are tested, the dielectric strength may be determined by dividing the minimum breakdown voltage by the average dielectric thickness.

Equivalent Series Resistance (ESR)

Equivalence series resistance may be measured using a Keithley 3330 Precision LCZ meter with Kelvin Leads 2.2 volt DC bias and a 0.5 volt peak to peak sinusoidal signal. The operating frequency may 100 kHz and the temperature may be 23° C.±2° C.

Dissipation Factor

The dissipation factor may be measured using a Keithley 3330 Precision LCZ meter with Kelvin Leads with 2.2 volt DC bias and a 0.5 volt peak to peak sinusoidal signal. The operating frequency may be 120 Hz and the temperature may be 23° C.±2° C.

Capacitance

The capacitance may be measured using a Keithley 3330 Precision LCZ meter with Kelvin Leads with 2.2 volt DC bias and a 0.5 volt peak to peak sinusoidal signal. The operating frequency may be 120 Hz and the temperature may be 23° C.±2° C. In some cases, the "wet-to-dry" capacitance can be determined. The "dry capacitance" refers to the capacitance of the part before application of the solid electrolyte, graphite, and silver layers, while the "wet capacitance" refers to the capacitance of the part after formation of the dielectric, measured in 14% nitric acid in reference to 1 mF tantalum cathode with 10 volt DC bias and a 0.5 volt peak to peak sinusoidal signal after 30 seconds of electrolyte soaking.

Leakage Current

Leakage current may be measured using a leakage test meter at a temperature of 23° C.±2° C. or 125° C.±3° C. and at the rated voltage (e.g., 16 volts) after a minimum of 30 minutes.

Example 1

70,000 μFV/g tantalum powder was used to form anode samples. Each anode sample was embedded with a tantalum wire, sintered at 1300° C., and pressed to a density of 6.2 g/cm³. The resulting pellets had a size of 2.3×2.2×0.66 mm. The pellets were anodized to 30.5 volts in water/phosphoric acid electrolyte with a conductivity of 8.6 mS/cm at a temperature of 85° C. to form the dielectric layer. The pellets were anodized again to 50 volts in a water/boric acid/disodium tetraborate with a conductivity of 2.0 mS/cm at a temperature of 30° C. for 25 seconds to form a thicker oxide layer built up on the outside. A conductive polymer coating was then formed by dipping the anode into a butanol solution of iron (III) toluenesulfonate (Clevios™ C, Heraeus) and consequently into 3,4-ethylenedioxythiophene (Clevios™ M, Heraeus) and polymerized. After 45 minutes of polymerization, a thin layer of poly(3,4-ethylenedioxythiophene) was formed on the surface of the dielectric. The anode was washed in methanol to remove reaction by-products, anodized in a liquid electrolyte, and washed again in methanol. This process was repeated 6 times. Thereafter, the parts were dipped into a dispersed poly(3,4-ethylenedioxythiophene) having a solids content of 2.0% and viscosity 20 mPa·s (Clevios™ K, Heraeus). Upon coating, the parts were dried at 125° C. for 20 minutes. This process was repeated 3 times. Thereafter, the parts were dipped into a dispersed poly(3,4-ethylenedioxythiophene) having a solids content of 2.0% and viscosity 160 mPa·s (Clevios™ K, Heraeus). Upon coating, the parts were dried at 125° C. for 20 minutes. This process was repeated 14 times. The parts were then dipped into a graphite dispersion and dried. Finally, the parts were dipped into a silver dispersion and dried. Multiple parts (500) of 47 μF/16V capacitors were made in this manner and encapsulated in a standard silica resin.

Example 2

Capacitors were formed in the manner described in Example 1, except that a conductive polymer coating was formed by dipping the anode into a butanol solution of iron (III) toluenesulfonate (Clevios™ C, Heraeus) and consequently into a mixture of 3,4-ethylenedioxythiophene and 2-ethyl-3,4-ethylenedioxythiophene and polymerized. Multiple parts (500) of 47 μF/16V capacitors were made in this manner and encapsulated in a standard silica resin.

Example 3

Capacitors were formed in the manner described in Example 1, except that a conductive polymer coating was formed by dipping the anode into a butanol solution of iron (III) toluenesulfonate (Clevios™ C, Heraeus) and consequently into a mixture of 3,4-ethylenedioxythiophene and 2-butyl-3,4-ethylenedioxythiophene and polymerized. Multiple parts (500) of 47 µF/16V capacitors were made in this manner and encapsulated in a standard silica resin.

The minimum, mean and maximum measured breakdown voltage ("BDV") values and average dielectric thickness are set forth below in Table 1.

TABLE 1

BDV, Dielectric Thickness And Dielectric Strength

| | Minimum BDV [V] | Average BDV [V] | Maximum BDV [V] | Average Dielectric Thickness [nm] | Dielectric Strength [V/nm] |
|---|---|---|---|---|---|
| Example 1 | 26.34 | 27.27 | 28.10 | 52.6 | 0.50 |
| Example 2 | 29.01 | 29.72 | 31.28 | 52.5 | 0.55 |
| Example 3 | 30.98 | 31.73 | 32.83 | 52.8 | 0.59 |

The results of leakage current measurement at room and high temperature are set forth below in Table 2.

TABLE 2

Leakage Current

| | Leakage Current Average @ 23° C. [µA] | Leakage Current Average @ 125° C. [µA] | Ratio DCL (125° C.)/ DCL (25° C.) |
|---|---|---|---|
| Example 1 | 3.70 | 36.43 | 9.85 |
| Example 2 | 2.44 | 18.83 | 7.73 |
| Example 3 | 2.82 | 16.14 | 5.72 |

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A capacitor comprising a capacitor element, the capacitor element comprising:
   a sintered porous anode body;
   a dielectric that overlies the anode body, wherein at least a portion of the dielectric at an external surface of the capacitor has a greater thickness than at least a portion at an interior surface of the capacitor; and
   a solid electrolyte that overlies the dielectric, wherein the solid electrolyte contains an inner layer and an outer layer, wherein the inner layer is formed from an in situ-polymerized conductive polymer and the outer layer is formed from pre-polymerized conductive polymer particles, wherein the in-situ polymerized conductive polymer is formed from 3,4-ethylenedioxythiophene and an alkylated thiophene monomer having the following general structure:

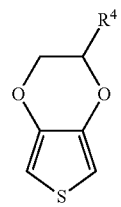

wherein, $R^4$ is an alkyl group, and
wherein the capacitor exhibits a leakage current at a temperature of 125° C. and a leakage current at a temperature of 23° C., wherein the ratio of the leakage current at 125° C. to the leakage current at 23° C. is about 8 or less; and
wherein the capacitor exhibits a dielectric strength of about 0.5 V/nm or more, wherein the dielectric has a thickness of from about 40 nm to about 100 nm.

2. The capacitor of claim 1, wherein $R^4$ is methyl, ethyl, propyl, or butyl.

3. The capacitor of claim 1, wherein the in-situ polymerized conductive polymer is formed by reacting the 3,4-ethylenedioxythiophene and the alkylated thiophene monomer with an oxidative catalyst.

4. The capacitor of claim 3, wherein the oxidative catalyst includes an iron (III) salt of an aromatic sulfonic acid.

5. The capacitor of claim 1, wherein the solid electrolyte contains from 2 to 30 inner layers that are formed from an in situ-polymerized conductive polymer.

6. The capacitor of claim 1, wherein the outer layer is formed from a dispersion of particles that contain a polymeric counterion and an extrinsically conductive polymer, wherein the extrinsically conductive polymer is poly(3,4-ethylenedioxythiophene).

7. The capacitor of claim 1, wherein the outer layer is formed from an intrinsically conductive polymer having repeating units of the following formula:

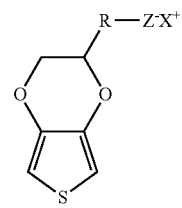

wherein,
R is $(CH_2)_a$—O—$(CH_2)_b$-L, where L is a bond or HC($[CH_2]_c$H);
a is from 0 to 10;
b is from 1 to 18;
c is from 0 to 10;
Z is an anion; and
X is a cation.

8. The capacitor of claim 1, wherein at least a portion of the pre-polymerized conductive polymer particles in the outer layer have an average size of from about 1 to about 80 nanometers.

9. The capacitor of claim 1, wherein the outer layer is generally free of in situ-polymerized conductive polymers.

10. The capacitor of claim 1, wherein the solid electrolyte contains from 2 to 30 outer layers that are formed from pre-polymerized conductive polymer particles.

11. The capacitor of claim 1, further comprising an external polymer coating that overlies the solid electrolyte and contains pre-polymerized conductive polymer particles and a cross-linking agent.

12. The capacitor of claim 11, wherein at least a portion of the conductive polymer particles in the external polymer coating have an average size of from about 80 to about 500 nanometers.

13. The capacitor of claim 1, wherein the anode body includes tantalum and the dielectric includes tantalum pentoxide.

14. The capacitor of claim 1, further comprising an anode termination that is in electrical connection with the anode body;
   a cathode termination that is in electrical connection with the solid electrolyte; and
   a housing that encloses the capacitor element and leaves exposed at least a portion of the anode termination and the cathode termination.

15. The capacitor of claim 14, wherein the housing is formed from a resinous material that encapsulates the capacitor element.

16. The capacitor of claim 14, wherein the housing defines an interior cavity within which the capacitor element is positioned, wherein the interior cavity has a gaseous atmosphere that includes an inert gas.

17. The capacitor of claim 1, wherein the capacitor exhibits a breakdown voltage of about 25 volts or more.

18. The capacitor of claim 1, wherein the capacitor exhibits a leakage current of about 3.5 $\mu$A or less at a temperature of 23° C.

19. A method for forming the capacitor of claim 1, the method comprising polymerizing the 3,4-ethylenedioxythiophene and the alkylated thiophene monomer in the presence of an oxidative catalyst to form the inner layer, thereafter applying a dispersion of conductive polymer particles to form the outer layer.

20. The method of claim 18, wherein the 3,4-ethylenedioxythiophene and the alkylated thiophene monomer, and the oxidative catalyst are sequentially applied.

21. The method of claim 18, wherein at least a portion of the conductive polymer particles have an average size of from about 1 to about 80 nanometers.

22. The capacitor of claim 1, wherein a weight ratio of alkylated thiophene monomer to the 3,4-ethylenedioxythiophene is from about 0.1:1 to about 1:0.1.

* * * * *